United States Patent
Kaiser et al.

(10) Patent No.: US 8,936,620 B2
(45) Date of Patent: Jan. 20, 2015

(54) METHOD AND APPARATUS FOR SECURING SOFT TISSUE TO BONE

(75) Inventors: William Kaiser, San Jose, CA (US); Jonathan Dewey, Sunnyvale, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 1029 days.

(21) Appl. No.: 12/177,082

(22) Filed: Jul. 21, 2008

(65) Prior Publication Data
US 2010/0016892 A1 Jan. 21, 2010

(51) Int. Cl.
*A61B 17/04* (2006.01)

(52) U.S. Cl.
CPC ..... *A61B 17/0401* (2013.01); *A61B 2017/0409* (2013.01); *A61B 2017/0412* (2013.01); *A61B 2017/0414* (2013.01); *A61B 2017/0446* (2013.01); *A61B 2017/0451* (2013.01); *A61B 2017/0456* (2013.01); *A61B 2017/0459* (2013.01); *A61B 2017/0461* (2013.01); *A61B 2017/0496* (2013.01)
USPC ............................ 606/232; 606/300; 606/323

(58) Field of Classification Search
USPC ........... 606/60, 104, 139, 144, 228, 232, 300, 606/323, 148; 128/898; 623/13.14, 17.16
See application file for complete search history.

(56) References Cited

U.S. PATENT DOCUMENTS

| | | | | |
|---|---|---|---|---|
| 5,224,946 | A * | 7/1993 | Hayhurst et al. | 606/232 |
| 7,867,251 | B2 * | 1/2011 | Colleran et al. | 606/232 |
| 8,231,654 | B2 * | 7/2012 | Kaiser et al. | 606/232 |
| 2002/0095180 | A1 * | 7/2002 | West et al. | 606/228 |
| 2002/0173822 | A1 * | 11/2002 | Justin et al. | 606/232 |
| 2003/0060835 | A1 * | 3/2003 | Wenstrom, Jr. | 606/148 |
| 2003/0065361 | A1 * | 4/2003 | Dreyfuss | 606/232 |
| 2003/0105524 | A1 * | 6/2003 | Paulos et al. | 623/13.14 |
| 2003/0120309 | A1 * | 6/2003 | Colleran et al. | 606/232 |
| 2003/0130694 | A1 * | 7/2003 | Bojarski et al. | 606/228 |

(Continued)

*Primary Examiner* — Ashley Fishback
*Assistant Examiner* — Jing Ou
(74) *Attorney, Agent, or Firm* — Pandiscio & Pandiscio

(57) ABSTRACT

Apparatus for securing an object to bone, the apparatus comprising:
 a suture anchor assembly comprising a suture anchor body and a suture;
  the suture anchor body being configured to be lockingly disposed within a hole formed in the bone, and having an opening formed therein for slidably receiving the suture therethrough;
  the suture having a first end, a second end and an intermediate portion extending therebetween;
  the suture extending through the opening in the suture anchor body so that the intermediate portion forms a loop on one side of the opening and the first and second ends are disposed on the other side of the opening, such that when the first end of the suture is passed through the loop and securingly engages the object, pulling on the second end of the suture draws the loop and a captured portion of the suture along a path toward the opening in the suture anchor body;
  the suture anchor body being configured so that when the suture anchor body is disposed in the hole in the bone, a tapered binding zone is established along the path followed by the loop and the captured portion of the suture when the second end of the suture is pulled, the tapered binding zone having a successively decreasing cross-sectional area such that continued pulling of the second end of the suture causes the loop and the captured portion of the suture to be jammed tightly in the tapered binding zone, whereby to bind the suture, and hence the object, to the suture anchor body, which is itself lockingly disposed within the bone.

13 Claims, 42 Drawing Sheets

(56) References Cited

U.S. PATENT DOCUMENTS

| | | |
|---|---|---|
| 2004/0002734 A1* | 1/2004 | Fallin et al. .................. 606/232 |
| 2004/0034357 A1* | 2/2004 | Beane et al. .................... 606/73 |
| 2004/0093031 A1* | 5/2004 | Burkhart et al. .............. 606/232 |
| 2004/0106950 A1* | 6/2004 | Grafton et al. ................ 606/232 |
| 2004/0133239 A1* | 7/2004 | Singhatat ...................... 606/232 |
| 2004/0236373 A1* | 11/2004 | Anspach, III ................. 606/232 |
| 2005/0055052 A1* | 3/2005 | Lombardo et al. ............ 606/232 |
| 2005/0149122 A1* | 7/2005 | McDevitt et al. ............. 606/232 |
| 2006/0079904 A1* | 4/2006 | Thal ................................ 606/72 |
| 2006/0106423 A1* | 5/2006 | Weisel et al. .................. 606/232 |
| 2006/0122608 A1* | 6/2006 | Fallin et al. ...................... 606/72 |
| 2006/0161183 A1* | 7/2006 | Sauer ............................. 606/148 |
| 2006/0276841 A1* | 12/2006 | Barbieri et al. ................ 606/232 |
| 2006/0282083 A1* | 12/2006 | Fanton et al. .................... 606/72 |
| 2006/0293710 A1* | 12/2006 | Foerster et al. ................ 606/232 |
| 2007/0135843 A1* | 6/2007 | Burkhart ........................ 606/232 |
| 2007/0173845 A1* | 7/2007 | Kim ................................. 606/73 |
| 2007/0203498 A1* | 8/2007 | Gerber et al. .................... 606/72 |
| 2008/0103528 A1* | 5/2008 | Zirps et al. ..................... 606/232 |
| 2008/0255613 A1* | 10/2008 | Kaiser et al. .................. 606/232 |

\* cited by examiner

Anchor (w/o taper ridges) w/suture passed through

The anchor in bone. The second picture shows passing the pass-thru end through the loop As the tightening end is pulled, the loop pulls the pass-thru into the device

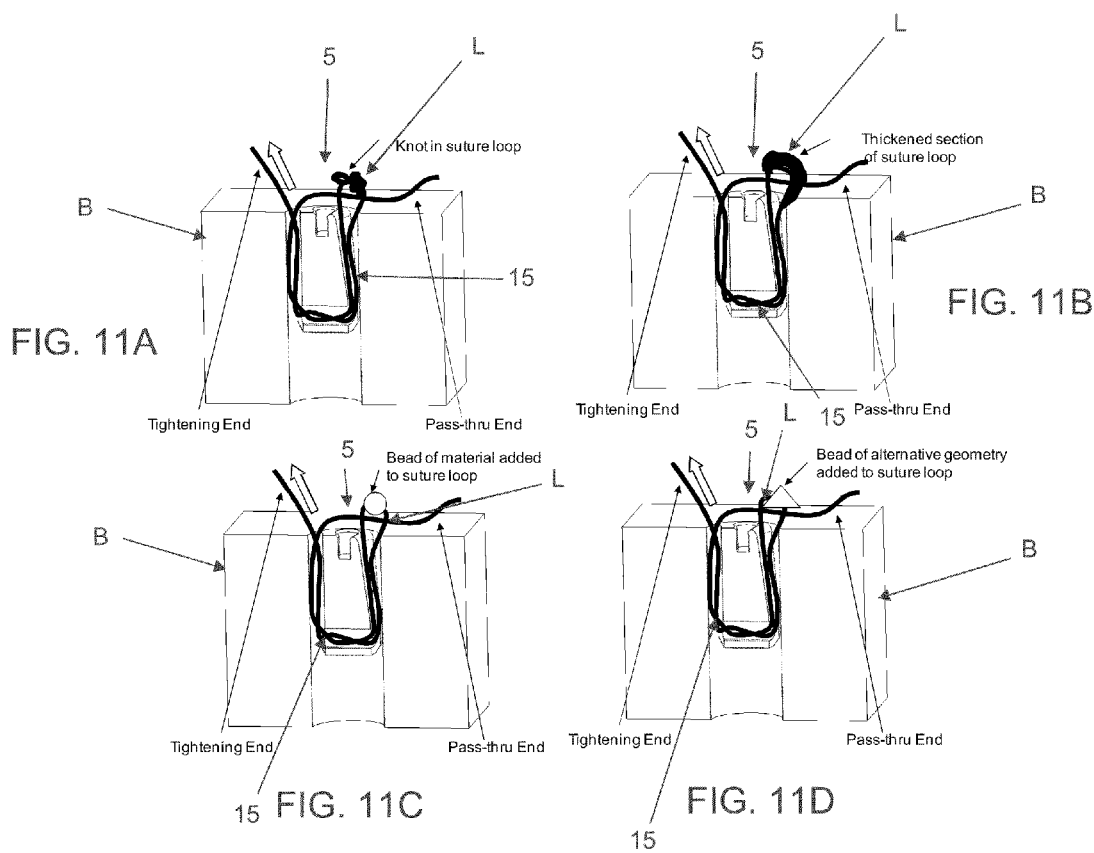

Figs. 12-14: Variations of Suture Throw Disposed External To, And Laterally Of, Anchor Body - Tapered Crossbore With Conical Geometry
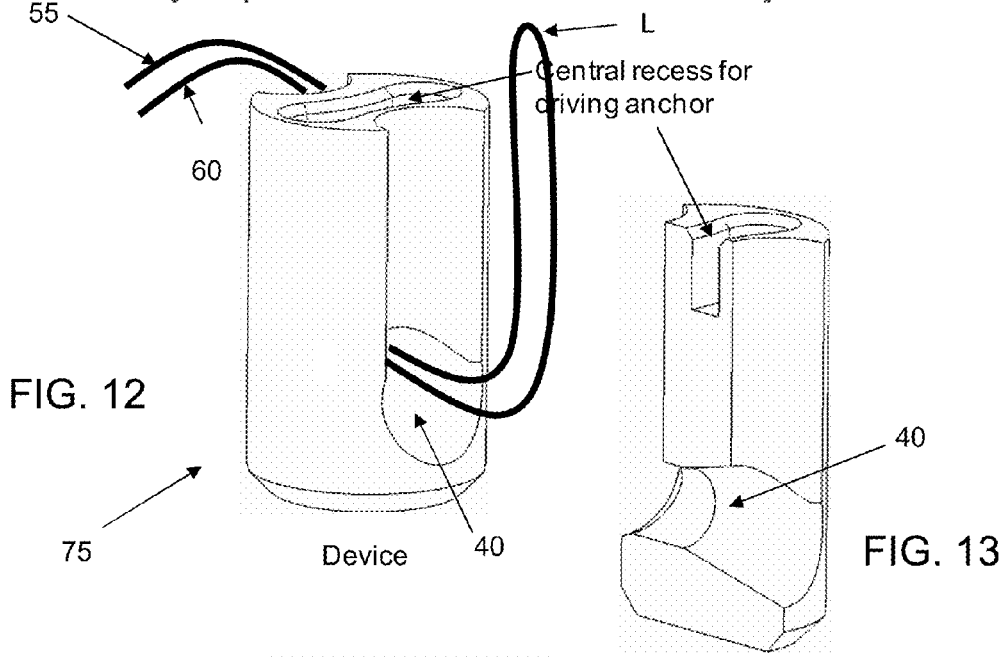
FIG. 12
FIG. 13
Device (Sectioned)
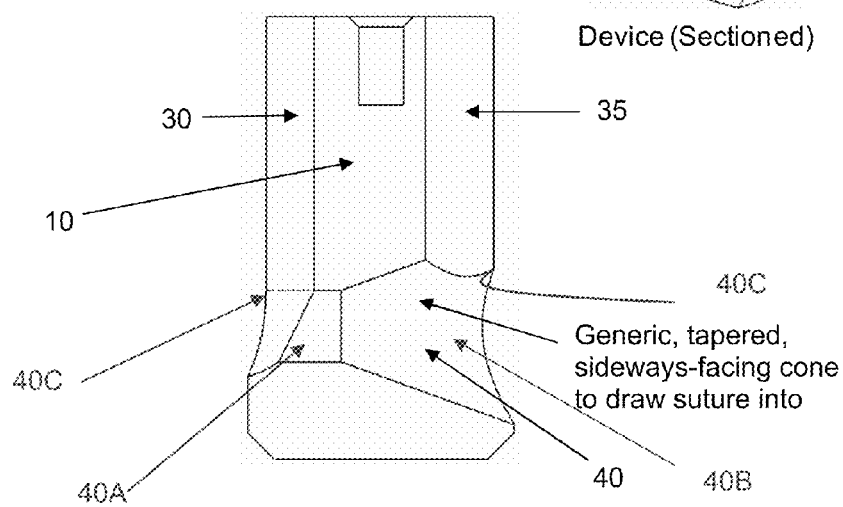
FIG. 14

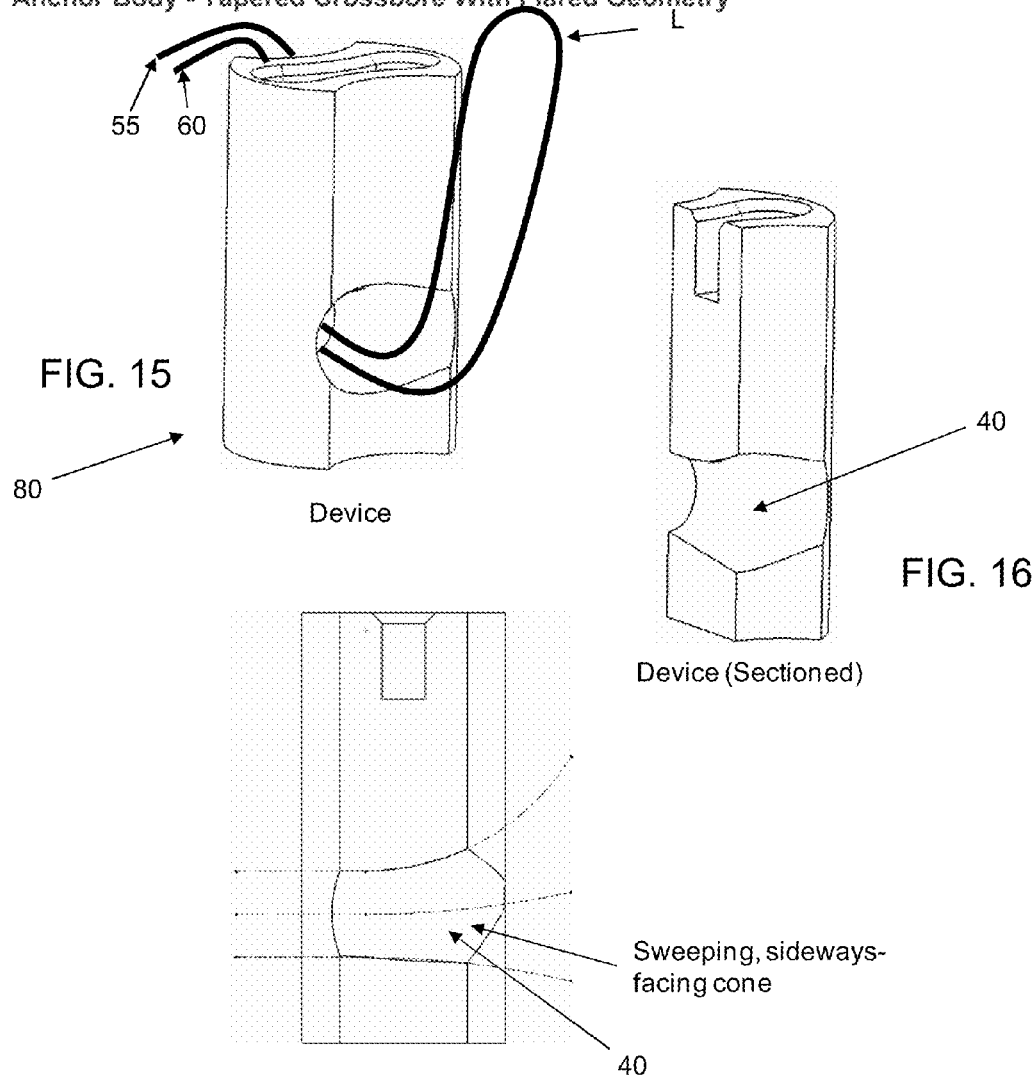

Tapered portion w/ridges. Ridges increase device's ability to lock the passed through portion of suture Fig. 24: Variations of Suture Throw Disposed External To, And Laterally Of, Anchor Body - Ribbed Suture Grooves And Anchor Body With Enhanced Pull-out Resistance Figs. 26-29: Suture Throw Disposed External To, And Laterally Of, Anchor Body, With Suture Path Starting Internal, Passing External And Returning Internal Figs. 30-32: Suture Throw Disposed Internal To Anchor Body, With Suture Path Starting Internal, Passing External (Two Paths) And Returning Internal Figs. 35-36: Suture Throw Disposed Internal To Anchor Body, With Suture Path Starting Internal, Passing Through And Around Distal End And Returning Internal Figs. 37-43: Variation Of Suture Throw Disposed Internal To Anchor Body, With Suture Path Starting Internal, Passing Through And Around Distal End And Returning Internal - Four Distal Holes
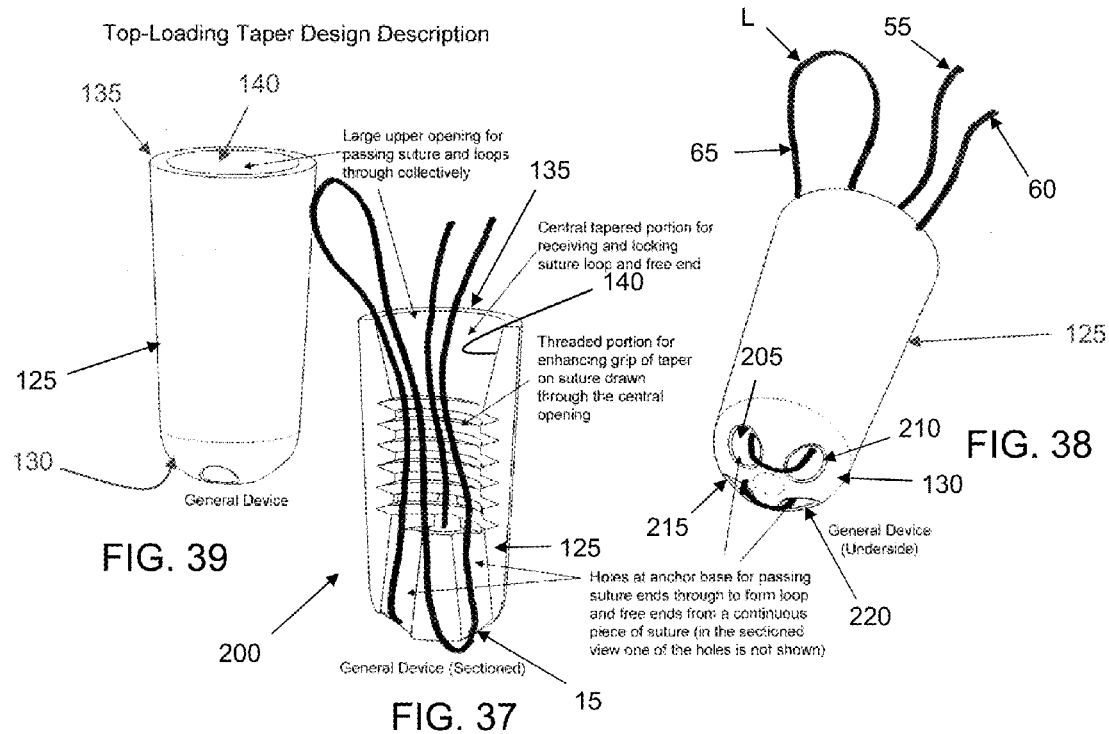

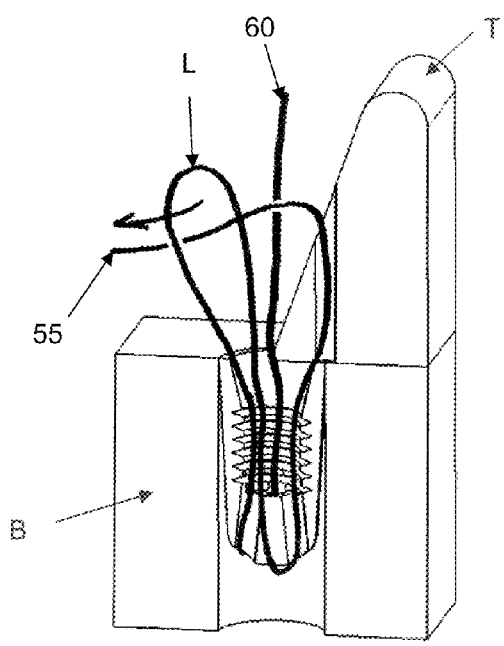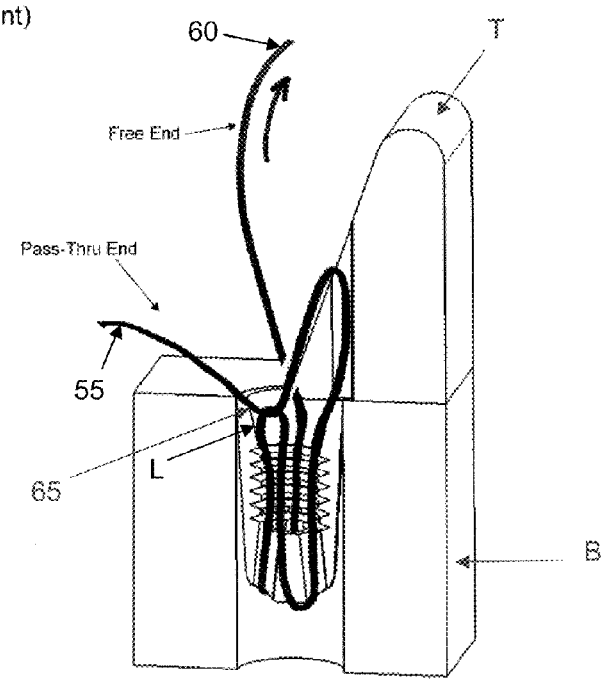
FIG. 42 — Step 3: Insert Passed End Through Open Loop
FIG. 43 — Step 4: Pull Free End of Suture, Drawing Loop and Passed End into the Central Taper

METHOD AND APPARATUS FOR SECURING SOFT TISSUE TO BONE

FIELD OF THE INVENTION

This invention relates to surgical methods and apparatus in general, and more particularly to surgical methods and apparatus for securing soft tissue to bone.

BACKGROUND OF THE INVENTION

Various types of soft tissue are normally attached to bone. By way of example but not limitation, ligaments connect bone to bone, and tendons connect muscle to bone. By way of further example but not limitation, the labrum is soft tissue which is connected to the rim of the acetabular cup (i.e., bone) so as to form a natural seal for the hip joint.

Such bone-connected soft tissues may become detached from their host bone as the result of injury and/or disease. By way of example but not limitation, a ligament or tendon or labrum may all be detached from bone due to a sports-related injury. A detached ligament or tendon can cause anatomical instability, impede proper motion of the joint and cause pain. A detached or damaged labrum can impede proper motion of the hip joint and cause pain in the hip. In all of these cases, as well as numerous others, the corrective treatment typically involves surgically re-attaching the soft tissue to bone.

In addition to the foregoing, in some cases it may be necessary to intentionally detach soft tissue from bone in order to provide a therapeutic treatment. In these situations it is generally necessary to thereafter re-attach the soft tissue to its host bone. By way of example but not limitation, where a patient suffers from a pincer-type femoroacetabular impingement (FAI) of the hip joint, it may be necessary to remove the overgrown portion of the acetabular rim in order to alleviate the pincer-type impingement. This generally involves surgically detaching the labrum from the acetabulum, debriding the underlying acetabular bone, and then re-attaching the labrum to the acetabulum.

Thus it will be seen that in many cases it may be necessary or desirable to attach (or re-attach) soft tissue to bone.

Historically, soft tissue has been attached (or re-attached) to bone using nails, screws, staples and suture extended through holes formed in the bone. All of these approaches suffered from a variety of deficiencies, including loosening, tissue necrosis, etc.

More recently, suture anchor assemblies have been used to secure soft tissue to bone. More particularly, these suture anchor assemblies generally have two suture strands attached to a suture anchor body, the suture anchor body is deployed in the bone, and then the suture strands are used to tie the soft tissue to the bone. This is done by passing one or more of the suture strands through the soft tissue, properly tensioning the suture, and then tying a knot (or knots) in the free ends of the suture so as to secure the soft tissue to the bone.

While such suture anchor assemblies have proven to be a major advance over earlier attachment techniques, they suffer from the serious disadvantage of requiring the surgeon to tie a knot (or knots) in the suture. More particularly, it can be time-consuming and technically challenging to form a tight knot in the suture, particularly during arthroscopic procedures where the soft tissue attachment needs to take place at a remote location within the interior of a joint. Such remote knot-tying is currently done by forming a suture throw outside the joint, sliding the suture throw down to the surgical site using a suture rundown tool, forming a second suture throw outside the joint, sliding that second suture throw down to the surgical site using the suture rundown tool, etc. until the knot is formed. It will be appreciated that, at best, this procedure is time-consuming and, at worst, results in a knot which may provide inadequate securement and/or improper tension to the soft tissue.

The present invention is intended to provide a novel suture anchor assembly which may be used to secure soft tissue to bone without requiring the surgeon to tie a knot (or knots) in the suture, and while permitting the surgeon to control the tension with which the soft tissue is secured to bone.

SUMMARY OF THE INVENTION

The present invention provides a novel suture anchor assembly which may be used to secure soft tissue to bone without requiring the surgeon to tie a knot (or knots) in the suture, and while permitting the surgeon to control the tension with which the soft tissue is secured to bone.

The present invention generally comprises a suture anchor assembly comprising a suture anchor body and a suture slidably secured to the suture anchor body. The suture anchor body is configured to be disposed within the bone, and the suture is configured to be passed through or around the soft tissue which is to be secured to the bone. The suture anchor body and the suture are configured for knotlessly binding the suture, whereby to secure the soft tissue to the host bone. In accordance with the present invention, knotless suture binding is achieved by pulling successively increasing volumes of suture into a tapered binding zone having a successively decreasing cross-sectional area so that the sliding suture is eventually jammed, and hence bound, in position.

In accordance with the present invention, the tapered binding zone can be provided (i) external to the suture anchor body, by the creation of a tapered gap between the suture anchor body and the host bone, and/or (ii) internal to the suture anchor body, by providing a tapered binding zone within the suture anchor body itself.

In one form of the present invention, there is provided apparatus for securing an object to bone, the apparatus comprising:

a suture anchor assembly comprising a suture anchor body and a suture;

the suture anchor body being configured to be lockingly disposed within a hole formed in the bone, and having an opening formed therein for slidably receiving the suture therethrough;

the suture having a first end, a second end and an intermediate portion extending therebetween;

the suture extending through the opening in the suture anchor body so that the intermediate portion forms a loop on one side of the opening and the first and second ends are disposed on the other side of the opening, such that when the first end of the suture is passed through the loop and securingly engages the object, pulling on the second end of the suture draws the loop and a captured portion of the suture along a path toward the opening in the suture anchor body;

the suture anchor body being configured so that when the suture anchor body is disposed in the hole in the bone, a tapered binding zone is established along the path followed by the loop and the captured portion of the suture when the second end of the suture is pulled, the tapered binding zone having a successively decreasing cross-sectional area such that continued pulling of the second end of the suture causes the loop and the captured portion of the suture to be jammed tightly in the tapered binding zone, whereby to bind the suture, and hence the object, to the suture anchor body, which is itself lockingly disposed within the bone.

In another form of the present invention, there is provided a method for securing an object to bone, the method comprising:

providing an apparatus comprising:
a suture anchor assembly comprising a suture anchor body and a suture;
the suture anchor body having an opening formed therein for slidably receiving the suture therethrough;
the suture having a first end, a second end and an intermediate portion extending therebetween;
the suture extending through the opening in the suture anchor body so that the intermediate portion forms a loop on one side of the opening and the first and second ends are disposed on the other side of the opening;
the suture anchor body being configured so that when the suture anchor body is disposed in the hole in the bone, a tapered binding zone is established, the tapered binding zone having a successively decreasing cross-sectional area;

lockingly positioning the suture anchor body within the hole formed in the bone;

passing the first end of the suture through the loop and securingly engaging the object;

pulling on the second end of the suture so as to draw the loop and a captured portion of the suture into the tapered binding zone so as to cause the loop and the captured portion of the suture to be jammed tightly in the tapered binding zone, whereby to bind the suture, and hence the object, to the suture anchor body, which is itself lockingly disposed within the bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 11A-11D are schematic views showing how additional mass and bulk may be added to a portion of the suture in order to enhance locking of the suture;

FIGS. 12-14 are schematic views showing a second suture anchor assembly formed in accordance with the present invention;

FIGS. 15-17 are schematic views showing a third suture anchor assembly formed in accordance with the present invention;

FIGS. 37-43 are schematic views showing a twelfth suture anchor assembly formed in accordance with the present invention.

DETAILED DESCRIPTION OF THE INVENTION

Figure 1:
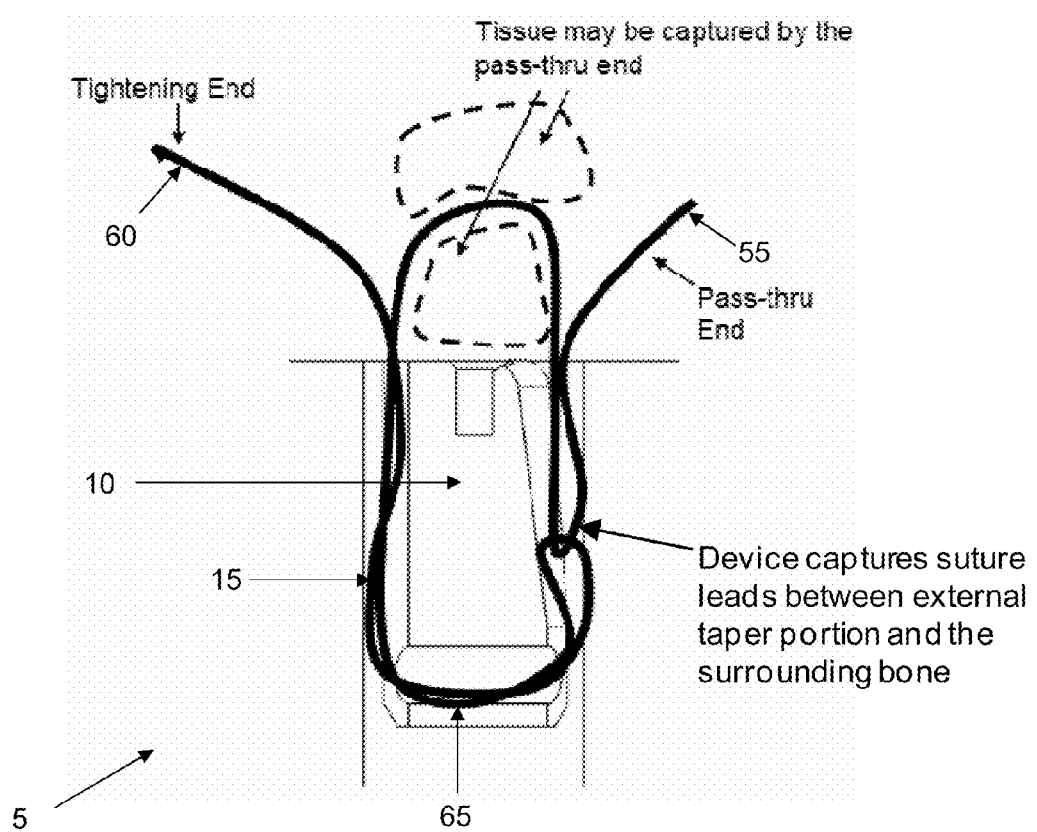
FIGS. 1-11 are schematic views showing a first suture anchor assembly formed in accordance with the present invention.
Figure 2:
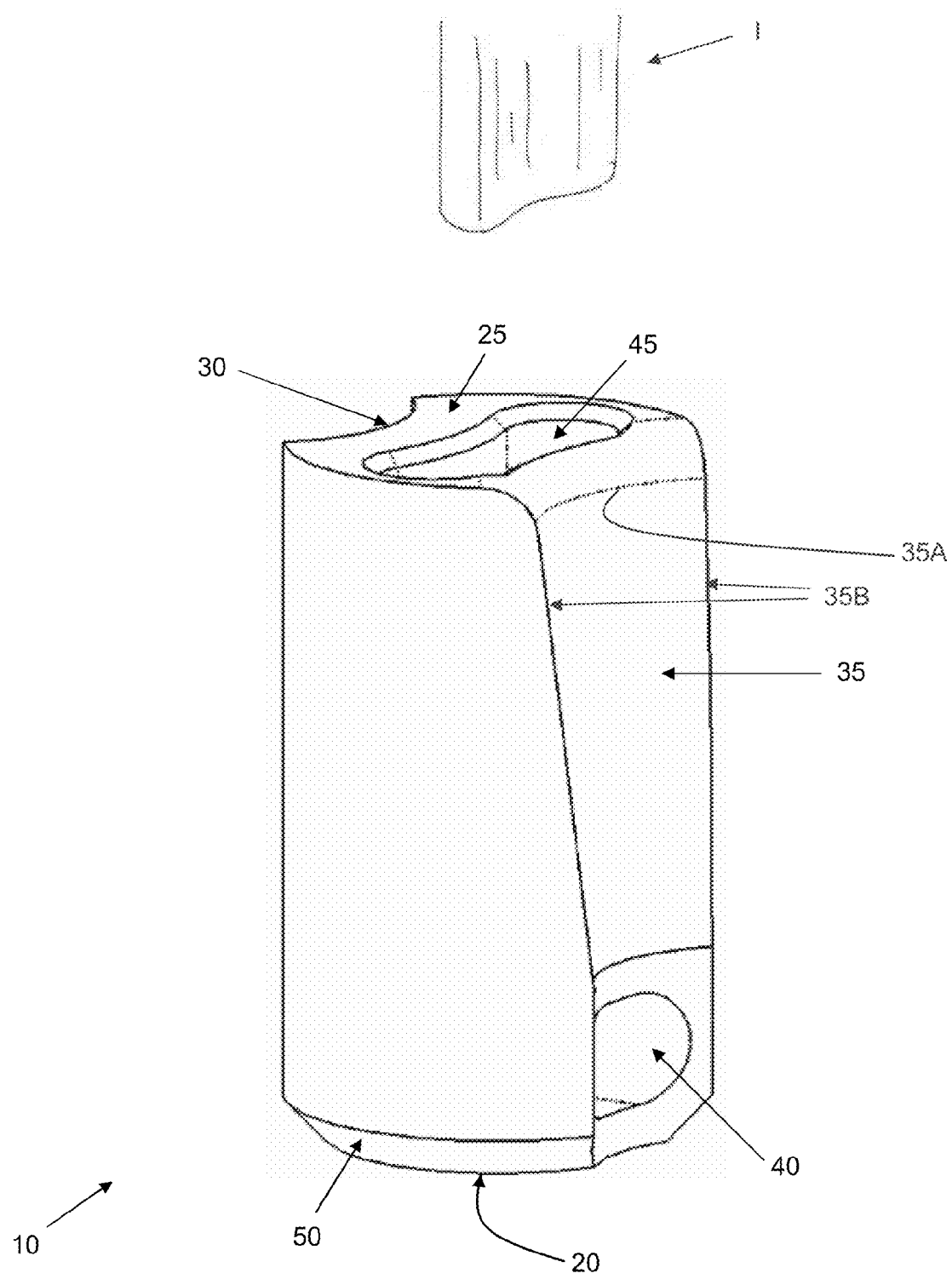
Figure 3:
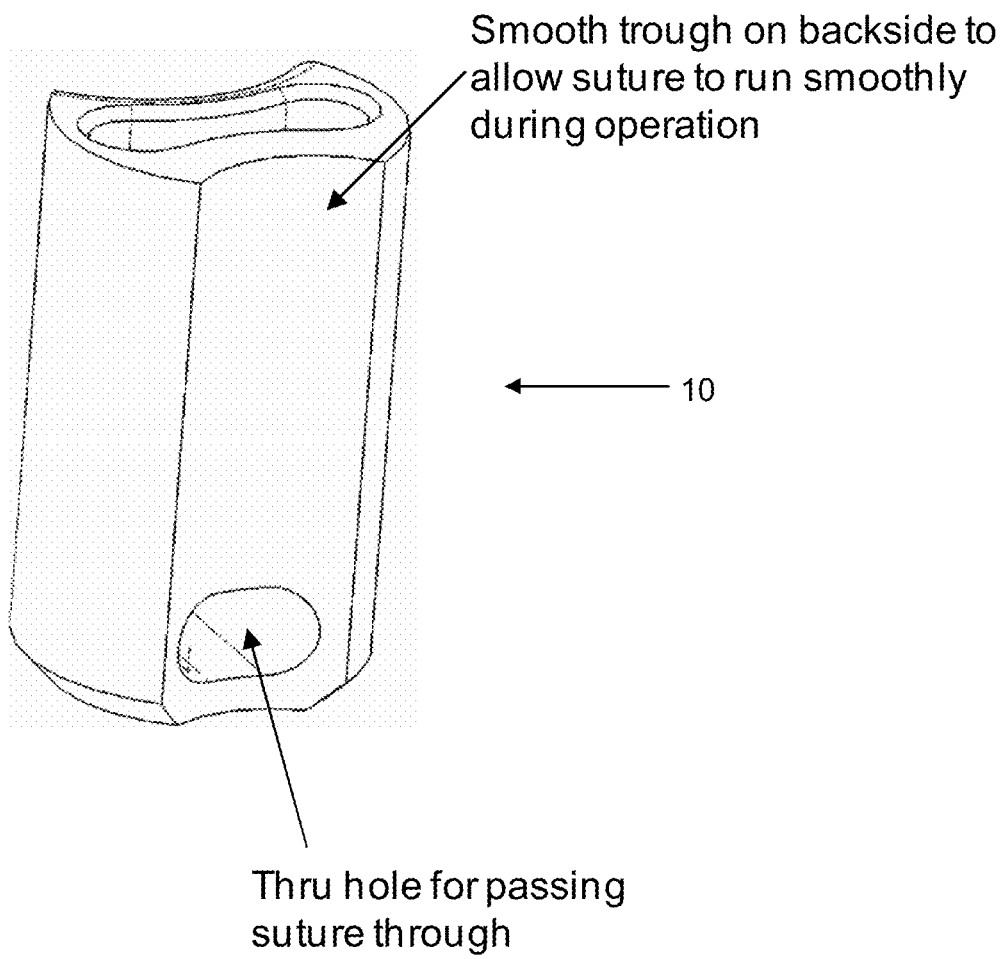
Figure 4:
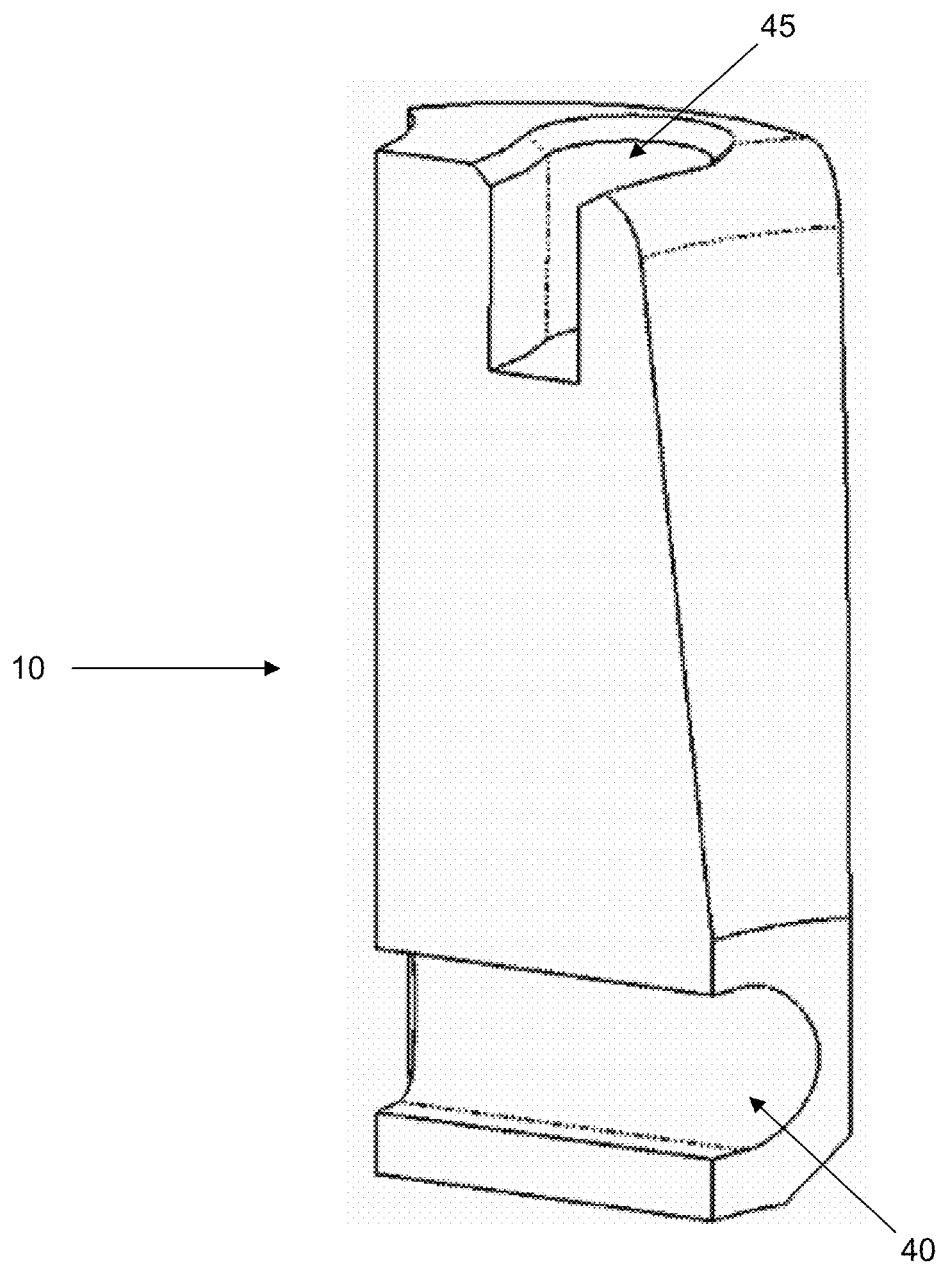

Looking first at FIGS. 1-5, there is shown a novel suture anchor assembly 5 which generally comprises a suture anchor body 10 and a suture 15. Suture anchor assembly 5 may be used to secure soft tissue to bone without requiring the surgeon to tie a knot (or knots) in the suture, and while permitting the surgeon to control the tension with which the soft tissue is secured to bone.

More particularly, suture anchor body 10 comprises a generally cylindrical structure having a distal end 20 and a proximal end 25. The side wall of suture anchor body 10 is provided with a pair of longitudinally-extending, diametrically-opposed recesses 30, 35.

Recess 35 preferably increases in depth as it approaches the proximal end of suture anchor body 10, and shallows in depth as it approaches the distal end of suture anchor body 10. With the disclosed locking mechanism, for the suture to be locked within the anchor, multiple strands of suture are pulled into an area smaller than the grouping of sutures, thereby causing knotless binding. In one preferred form of the invention, recess 35 has a depth adjacent to the proximal end of suture anchor body 10 which is greater than the thickness of the grouping of suture strands 15, and a depth adjacent to the distal end of suture anchor body 10 which is less than the thickness of the grouping of suture strands 15. In FIGS. 1-5, recess 35 is shown having a somewhat semi-circular cross-sectional shape, providing tapering in both the longitudinal (i.e., distal to proximal) direction and the lateral direction. In other words, a semi-circular recess 35 provides tapering at both the central portion 35A of recess 35 as well as at the edges 35B of recess 35. However, it should also be appreciated that recess 35 may be formed as a simple inclined flat plane, such that there is tapering in the longitudinal direction but not in the lateral direction. Furthermore, recess 35 may comprise a combination of different cross-sections along its length.

Figure 5:
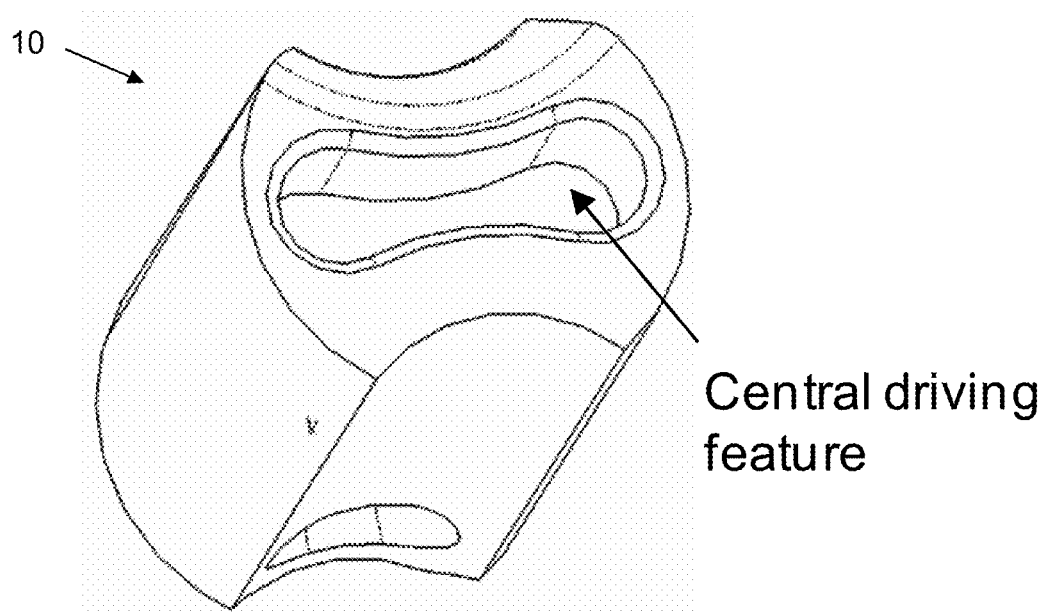
Figure 5A:
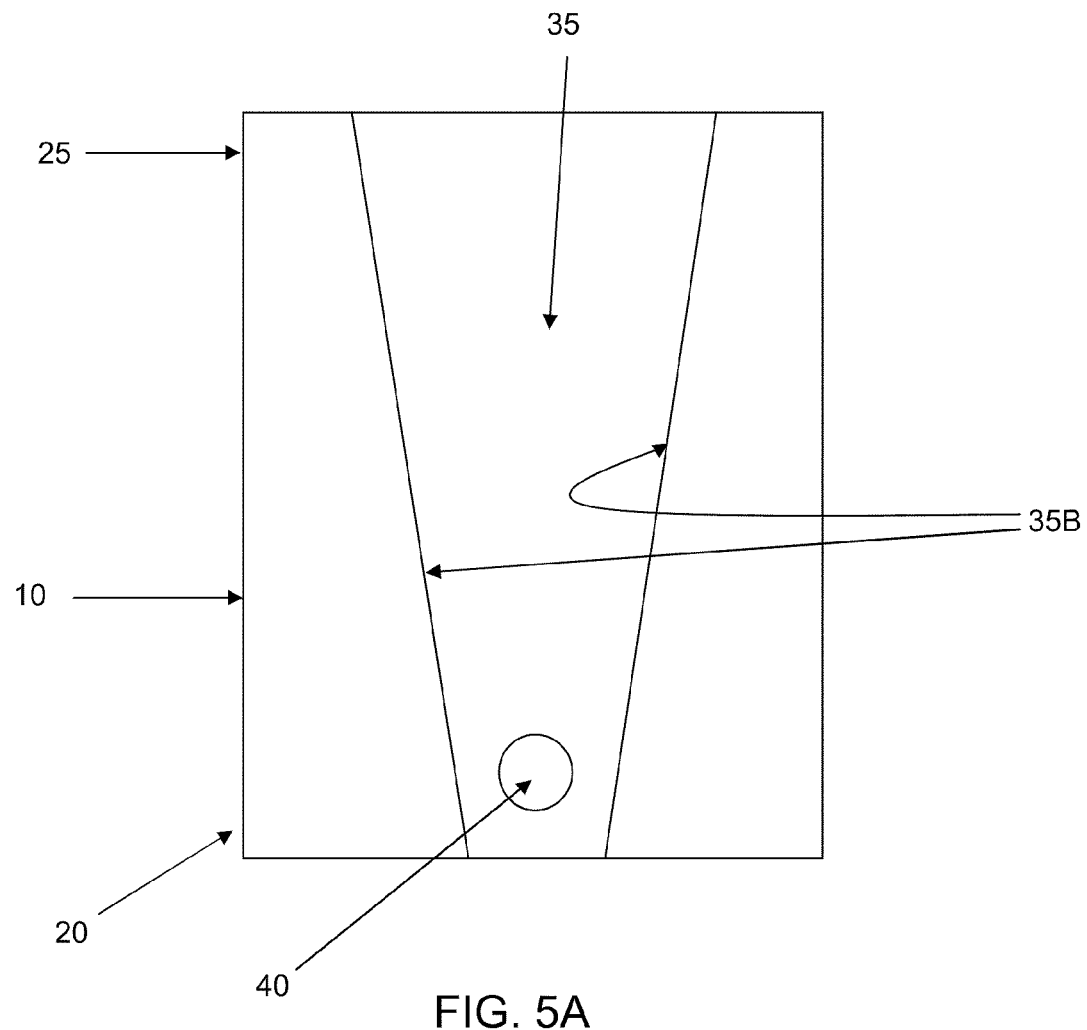
Figure 6:
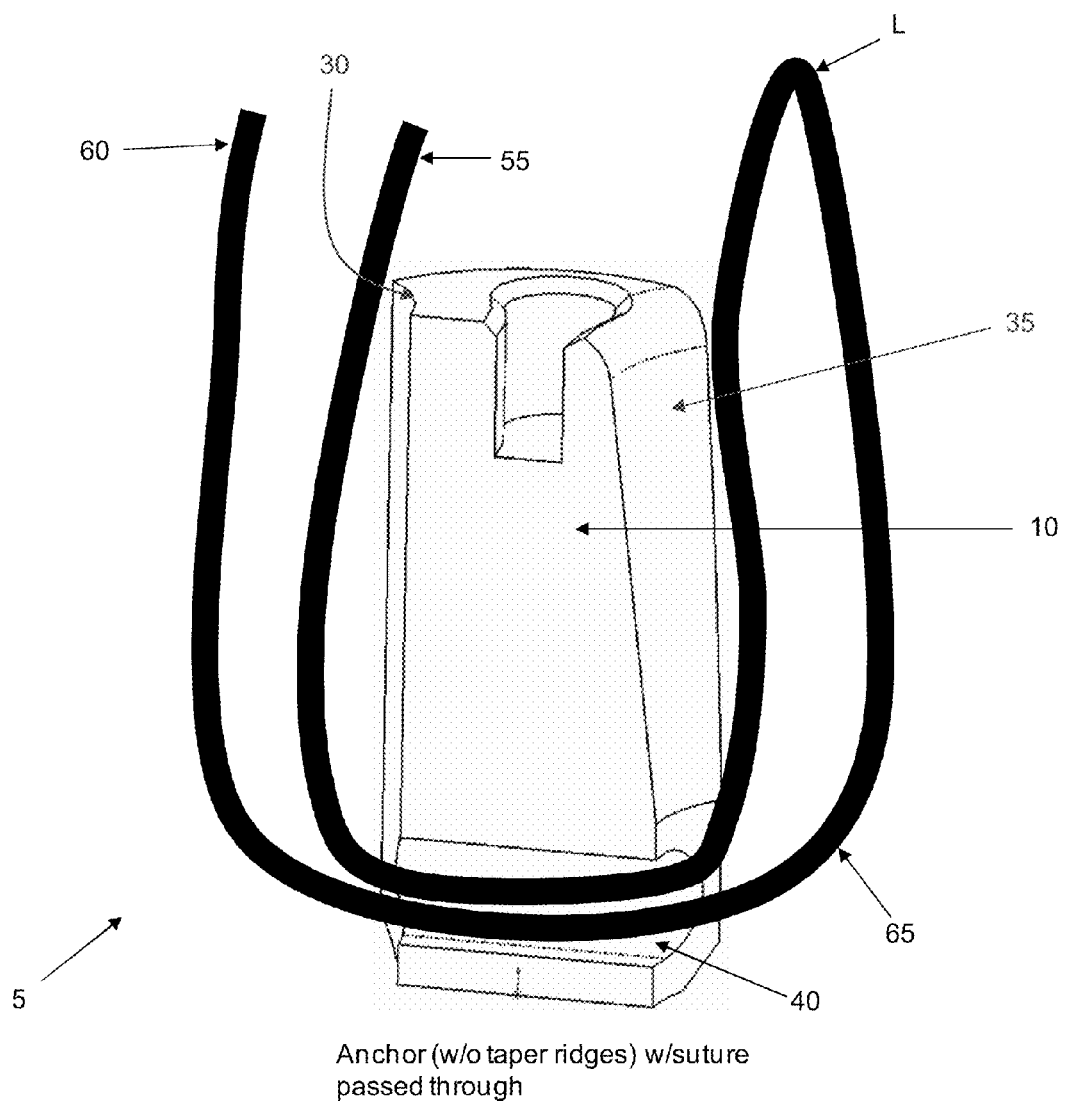

One variation to specifically note is providing recess 35 with or without a constant floor depth along the length of the recess, but with lateral walls tapering inwardly towards one another as they extend distally, thereby removing the need to lock suture 15 and loop L between bone B and suture body anchor 10, but using those surfaces as merely boundaries. See FIG. 5A.

It is also contemplated that variations of side-walled tapering/recess floor tapering may be utilized to effect suture binding.

Another variation for the system's tapering portion may include recess 35 having a constant floor depth for a portion of the recess, with a tapering floor portion (i.e., an inclined floor) for the remainder of recess 35. By using a combination of tapering sections and non-tapering sections, various cinching/binding areas can be achieved.

Recess 30 preferably extends parallel to the central axis of the body, i.e., it has a constant depth along the length of the recess. Recess 30 preferably also has a somewhat semi-circular cross-sectional shape, although it may also be formed as a simple flat plane.

A crossbore 40 extends between recesses 30, 35. Crossbore 40 is sized so as to slidingly receive suture 15 as will hereinafter be discussed in further detail.

The proximal end of suture anchor body 10 includes an opening 45 for receiving an inserter tool which may be used to deploy suture anchor assembly 5 in bone. Opening 45 is preferably shaped so as to minimize the amount of material removed from the central portion of the suture anchor body, which is where the deepest portion of recess 35 is located. Thus, to this end, where recess 35 and recess 30 have semi-circular cross-sections, opening 45 may be formed with an "hour-glass" (or "figure eight") cross-section. Additionally, by positioning the largest portions of opening 45 at the periphery of the suture anchor body, the inserter may be provided with matching lobes for driving the suture anchor assembly into bone. This construction can be advantageous, since mating the inserter and the suture anchor body more laterally (i.e., further outboard from the central longitudinal axis of the suture anchor body) provides a longer lever arm which permits more torque to be applied to the portion of the suture anchor body where more material is present.

Furthermore, by positioning crossbore 40 and opening 45 remote from one another (i.e., by positioning crossbore 40 at the distal end of the anchor body and positioning opening 45 at the proximal end of the anchor body), more material is available on the proximal end of the anchor body to support the anchor body/inserter interface. Separating the two features (i.e., crossbore 40 and opening 45) also provides more material to resist pullout of the suture through the anchor body.

If desired, the distal end of suture anchor body 10 may be tapered, e.g., as shown at 50, so as to facilitate insertion of the suture anchor assembly into bone.

Suture 15 comprises a single strand of suture having a leading end (also known as a "pass-thru end") 55, a trailing end (also know as a "tightening end") 60 and an intermediate portion 65 extending therebetween.

Looking next at FIGS. 6-11, suture anchor assembly 5 may be used in the following manner to secure soft tissue to bone without requiring the surgeon to tie a knot (or knots) in the suture.

More particularly, leading end 55 of suture 15 is first placed adjacent to trailing end 60 of suture 15, thereby forming a loop L in the intermediate portion 65 of suture 15. Then, loop L is threaded through crossbore 40, so that leading end 55 and trailing end 60 are disposed in recess 30 on one side of suture anchor body 10 and loop L is disposed in recess 35 on the other side of suture anchor body 10. See FIG. 6.

In an alternative embodiment, another transverse hole (not shown) more proximal to transverse hole 40 could be provided in suture anchor body 10, such that one or both of leads 55 and/or 60 could be directed back to the loop L side of the suture anchor body, i.e., so that one or both of leads 55 and/or 60 could be directed back into recess 35 and brought adjacent to loop L. This approach may be used to consolidate the leads/loop adjacent to one another, or to help increase identification for which leads 55, 65 control which function. It should be understood that this feature may also be adapted to other forms of the present invention (see below) where loop L and leads 55, 60 are on opposing sides of the suture anchor.

Then suture anchor assembly 5 is deployed in a bone B, preferably by advancing the distal end of suture anchor assembly 5 into a bone hole H formed in bone B. See FIG. 7. This may be done by mounting the distal end of an inserter I (FIG. 2) in opening 45 in suture anchor body 10, and simultaneously pulling a slight tension on (i) loop L and (ii) leading end 55 and trailing end 60, so that suture 15 is seated in recesses 30, 35. Then the inserter is used to push suture anchor assembly 5 into bone hole H.

Figure 7:
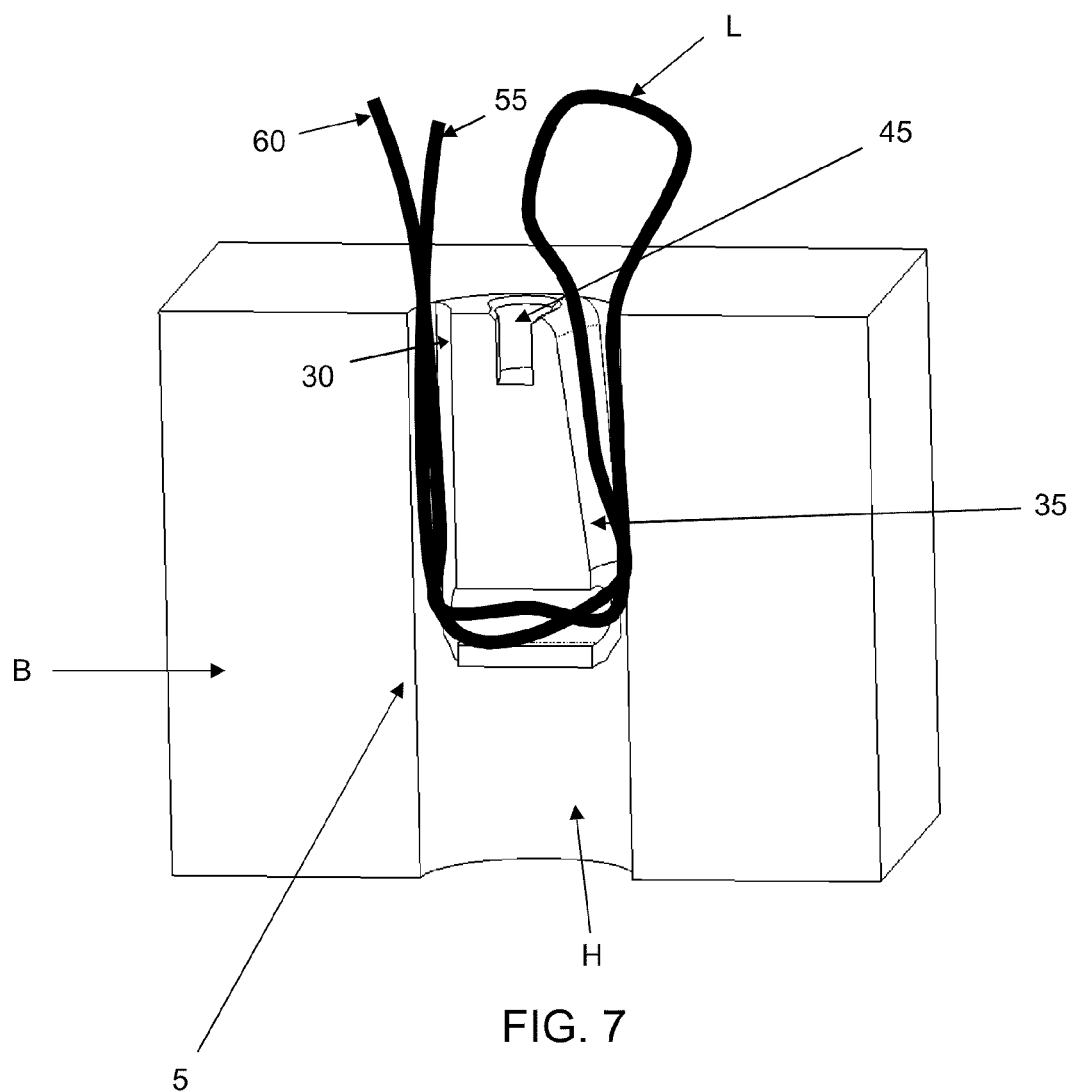
Figure 7A:
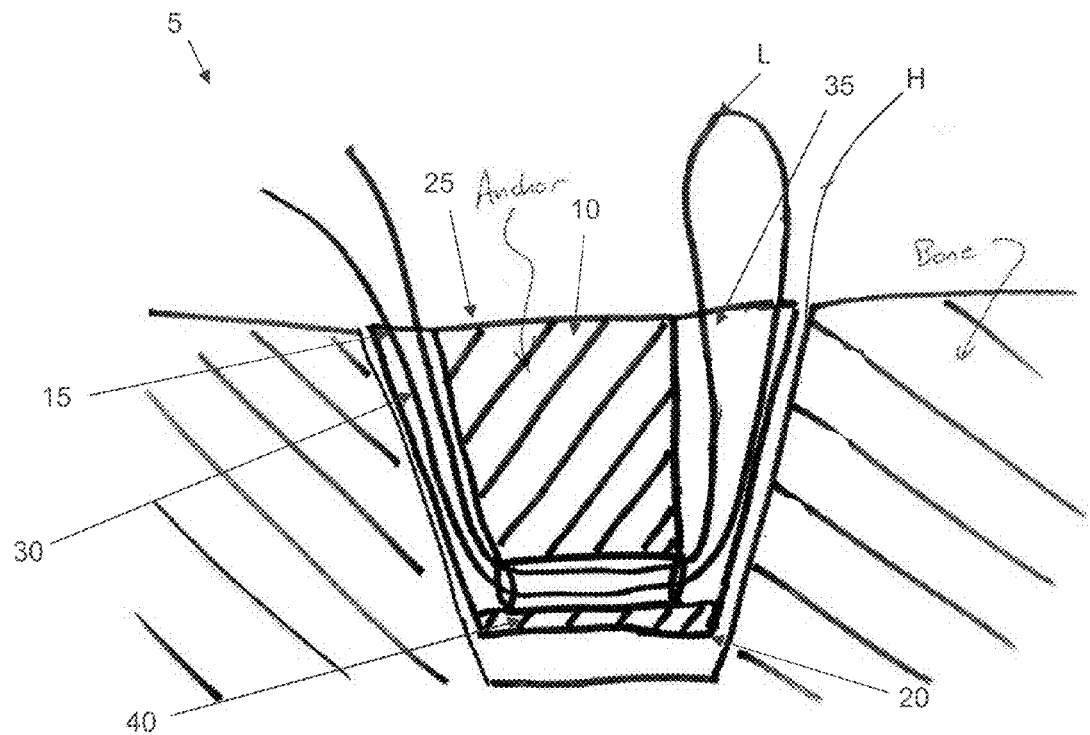
Figure 8:
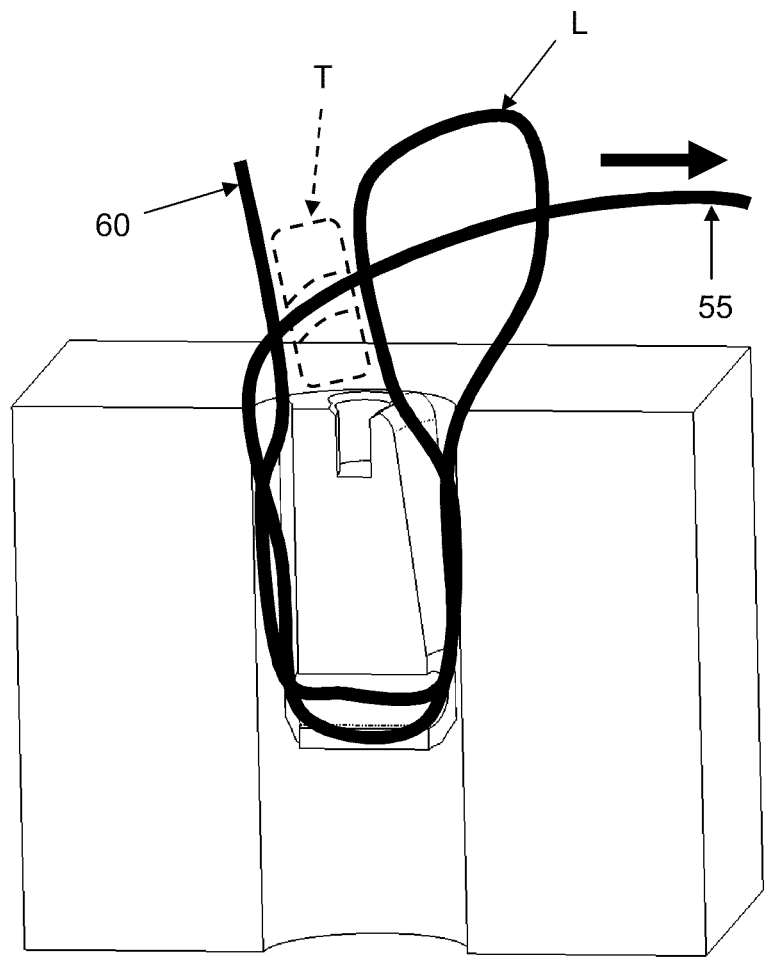
Figure 9:
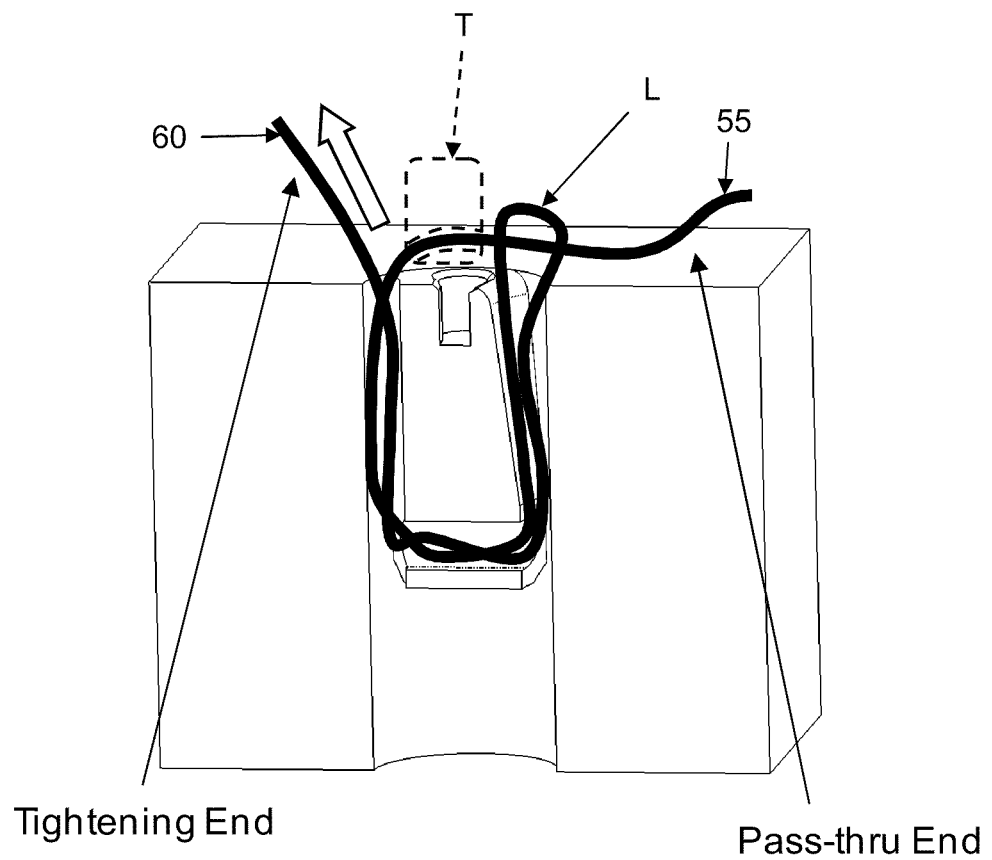
Figure 10:
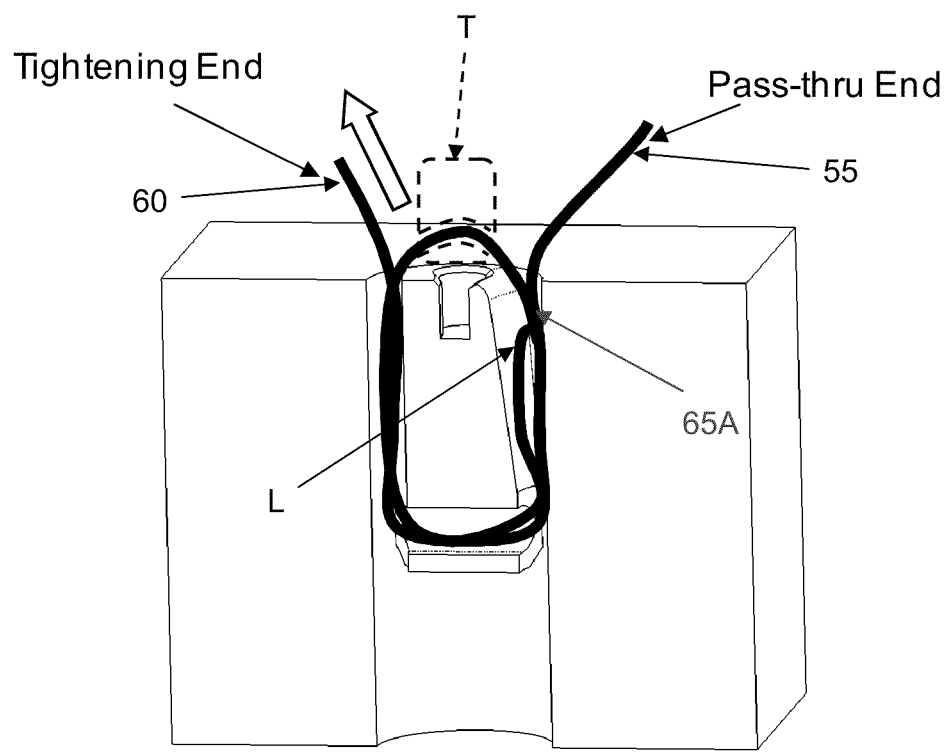
Figure 11:
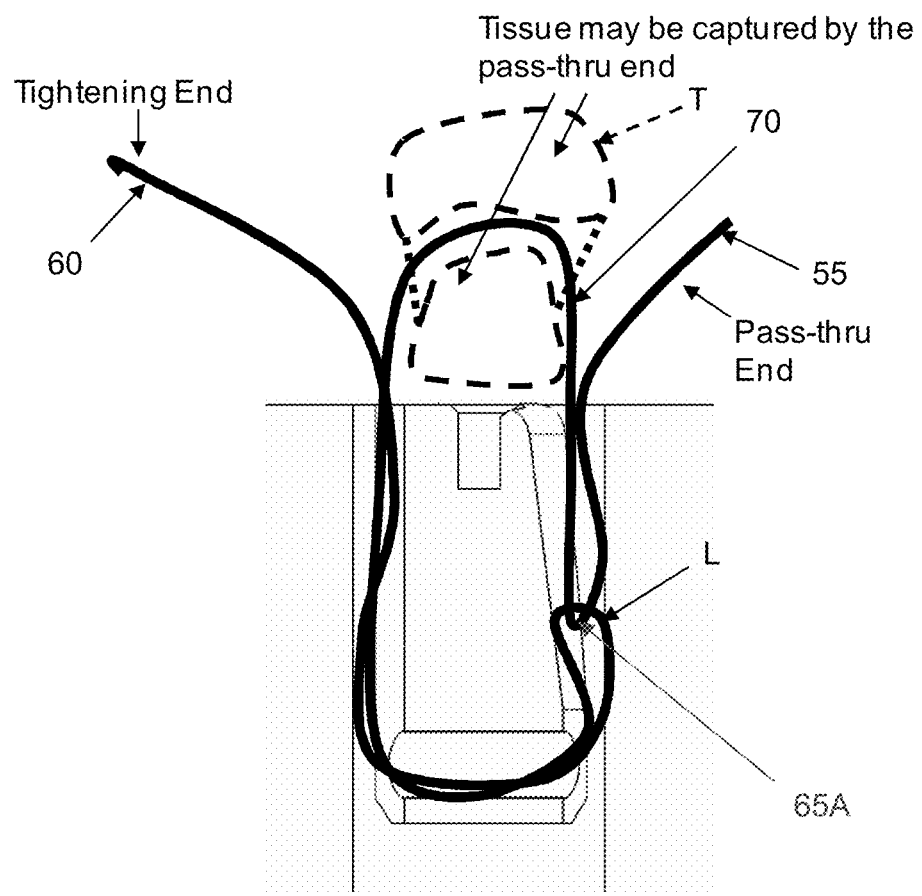

It will be appreciated that inasmuch as the depth of recess 35 decreases adjacent to the distal end of suture anchor body 10, the gap between the floor of recess 35 and the wall of bone hole H (i.e., the space for receiving suture 15) progressively narrows towards the distal end of suture anchor body 10. In an alternative embodiment, recess 35 could be formed so that it extends substantially parallel to the axis of suture anchor body 10, but bone hole H might be tapered (see FIG. 7A). In either case, it will be appreciated that the space between the floor of recess 35 and the wall of bone hole H progressively narrows towards the distal end of suture anchor body 10.

Next, leading end 55 is passed over (or through) tissue T and then through loop L. See FIG. 8.

Then, with leading end 55 held under tension, trailing end 60 is pulled. This action causes loop L and a portion 65A of the suture trailing leading end 55 to be drawn progressively deeper into bone hole H, and hence progressively deeper into the narrowing gap formed between suture anchor body 10 and bone B. See FIGS. 9-11. Thus, the more that trailing end 60 is pulled, the farther that loop L and suture portion 65A is pulled into the narrowing gap between suture anchor body 10 and bone B. Further pulling of trailing end 60 effectively jams loop L and suture portion 65A between suture anchor body 10 and bone B, thereby binding the suture at this location. This action effectively results in a fixed length 70 of suture 15 extending from loop L, over (or through) tissue T, and then back to loop L, with loop L being locked in position relative to the bone. Thus, by holding leading end 55 of suture 15 under tension and pulling trailing end 60 of suture 15 until loop L is locked in position between suture anchor body 10 and bone B, tissue T can be secured to bone B without requiring the surgeon to tie a knot (or knots) in the suture.

Stated differently, suture 15 is secured to bone B by pulling loop L and suture portion 65A into the narrowing gap formed between suture anchor body 10 and bone B until the suture is effectively jammed in place, thereby forming a knotless fixation.

It should be appreciated that it may be possible to improve the binding of suture 15 to bone B by adding mass and bulk to the portion of the suture which is drawn down into the narrowing gap formed between suture anchor body 10 and bone B. See, for example, FIGS. 11A, 11B, 11C and 11D. In these examples, additional mass and bulk is added to a portion of suture loop L. This additional mass and bulk helps the suture to more repeatably and controllably lock into the narrowing taper formed between suture anchor body 10 and bone B. In FIG. 11A, the additional mass and bulk is added by simply pre-knotting (e.g., at the time of manufacture) suture 15 at loop L. In FIG. 11B, the suture diameter is made thicker by overmolding, weaving or the addition of extra material to the suture, with the particular technique used depending the nature of the suture material and manufacturing preference. Thus, for example, where the suture is braided suture, the additional material may be deposited by overmolding on the braided suture or by additional weaving. Alternatively, where the suture is extruded monofilament, the additional material may be deposited by overmolding. In FIG. 11C, a bead of material is secured to suture loop L so that the bead of material increases the mass and bulk of the suture. Again, the specific manner in which this is done may depend on suture material and manufacturing preference. Thus, where the suture is braided suture, the bead of material may be strung onto the braided suture and then fixed in place (e.g., by an adhesive). Alternatively, where the suture is monofilament suture, the bead of material may be secured to the suture by overmolding. In FIG. 11D, a bead of a specific geometry (e.g., non-circular, triangular, rectangular, etc.) is attached to suture loop L. If desired, the specific geometry may be sized and shaped to fit into a specific recess formed within suture anchor body 10 so as to improve suture locking. All of these, and other, approaches add mass and bulk to the suture which aides cinching and securement. It is understood that the bulking features could be rigidly attached to the suture, or the bulking features may merely surround the suture and be free to slide thereon. In this latter respect, it will be appreciated that threading the suture ends through crossbore 40 would effectively capture the free floating bulking feature onto loop L.

Additionally, it should be appreciated that all of these suture additions are described as being attached at suture loop L rather than on pass-thru end 55. These features may be on either, though it is more desirable to include them on the loop L portion since these suture additions do not interfere with passing pass-thru end 55 through tissue (e.g., if the suture additions were placed on pass-thru end 55, a larger hole would have to be made in the tissue to pass the suture, suture passage might be hindered, etc.). By increasing the bulk of suture loop L, the cinching and securement of the suture may be enhanced and more precisely controlled.

Looking next at FIGS. 12-14, there is shown a novel suture anchor assembly 75 also formed in accordance with the present invention. Suture anchor assembly 75 is substantially the same as suture anchor assembly 5 discussed above, and is used in substantially the same way, except that (i) crossbore 40 is formed with a narrow throat 40A and flares outwardly at 40B as it approaches recess 35, and (ii) recesses 30 and 35 are formed with a floor which extends generally parallel to the central axis of suture anchor body 10. By forming crossbore 40 with a narrow throat 40A which flares outwardly at 40B as it opens towards recess 35, a suture binding zone is formed at the intersection of crossbore throat 40A and crossbore flare 40B. As a result, when tightening end 60 is pulled, loop L and suture portion 65A are pulled down into the binding zone created at the intersection of crossbore throat 40A and crossbore flare 40B, whereupon they bind, securing the tissue to the bone anchor body and hence to the bone. By forming recesses 30, 35 with flat (i.e., non-tapered) floors, suture 15 may be slid more easily into, and out of, crossbore 40, whereby to facilitate binding loop L and suture portion 65A at the convergence of crossbore throat 40A and crossbore flare 40B. Additionally, corner edgebreaks 40C, located at the transition points between crossbore 40 and recess 30 and/or recess 35, may be added in order to reduce the wear of the suture by softening the transition between recesses 30, 35 and crossbore 40.

By establishing the narrowing gap of the suture binding zone of suture anchor assembly 75 within crossbore 40 (as opposed to establishing the suture binding zone of suture anchor assembly 5 in the gap between suture anchor body 10 and bone B), a significant benefit may be obtained. More particularly, by creating the narrowing gap of the suture binding zone within crossbore 40, consistent geometries are provided which ensure binding of the suture with the anchor. In contrast, the external locking (between the anchor body and bone) of suture anchor assembly 5 relies on bone B and bone hole H to be substantially consistent for each use, even though they are potentially variable in nature due to variations in bone quality, patient anatomy, disease, trauma, and the surgical technique used to prepare the bone hole. By providing the suture binding zone in a narrowing crossbore 40, it is also possible to eliminate the need to carefully size bone hole H relative to suture anchor body 10 in order to ensure proper suture securement.

An additional benefit of binding the suture within crossbore 40, rather than adjacent to the sidewall of suture anchor body, is that the suture anchor assembly can better resist loosening of the soft tissue relative to the bone anchor assembly. This is because the suture binding is located perpendicular to the axis of withdrawal (i.e., the longitudinal axis of the bone hole) rather than parallel to the axis of withdrawal.

Furthermore, positioning the binding zone within tapered crossbore 40 provides the bound suture with a surrounding support structure of substantial integrity, thereby making the securement more stable and resisting failure of the suture anchor assembly.

Furthermore, if desired, recesses 30 and 35 may be terminated adjacent to crossbore 40, so that the recesses do not run the full length of the suture anchor body. This construction can help protect the suture during suture anchor insertion, and can provide additional strength at the distal end of the suture anchor body.

Looking next at FIGS. 15-17, there is shown a novel suture anchor assembly 80 also formed in accordance with the present invention. Suture anchor assembly 80 is substantially the same as suture anchor assembly 75 discussed above, and is used in substantially the same way, except that crossbore 40 has a sweeping taper along its length, whereby to provide a gently narrowing gap of the suture binding zone. Again, this construction can provide a more suture-friendly configuration while still permitting operation of the present invention.

Figure 18:
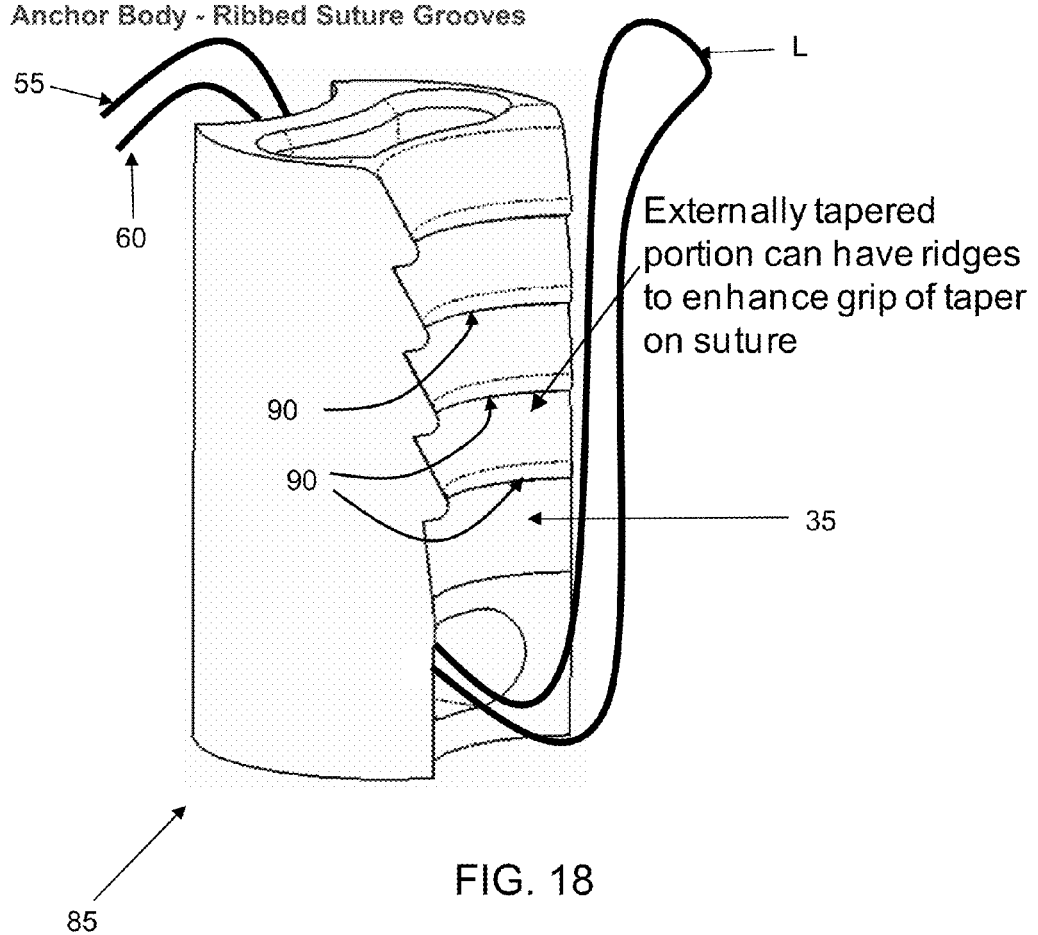
FIGS. 18-20 are schematic views showing a fourth suture anchor assembly formed in accordance with the present invention.
Figure 19:
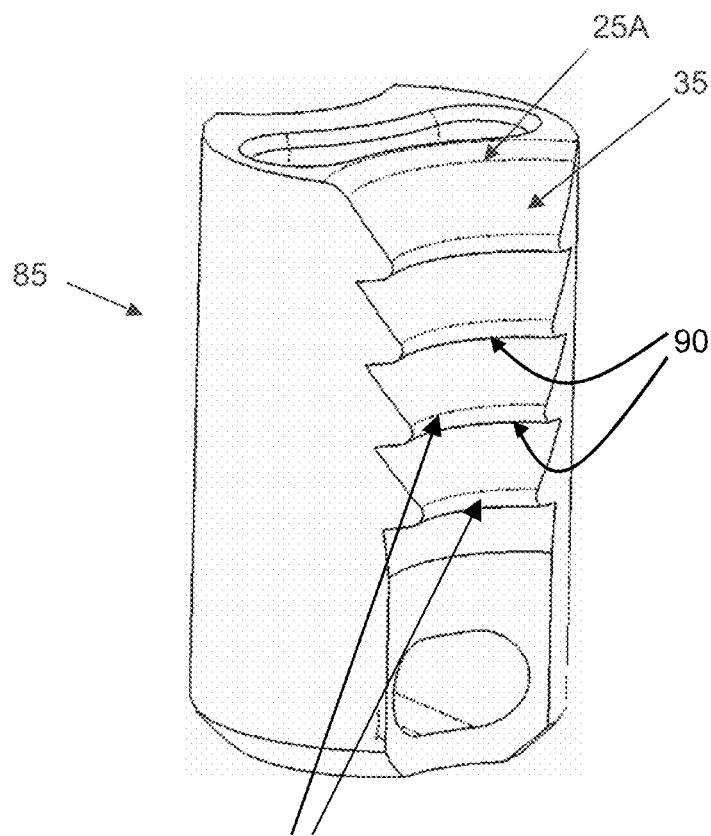
Figure 20:
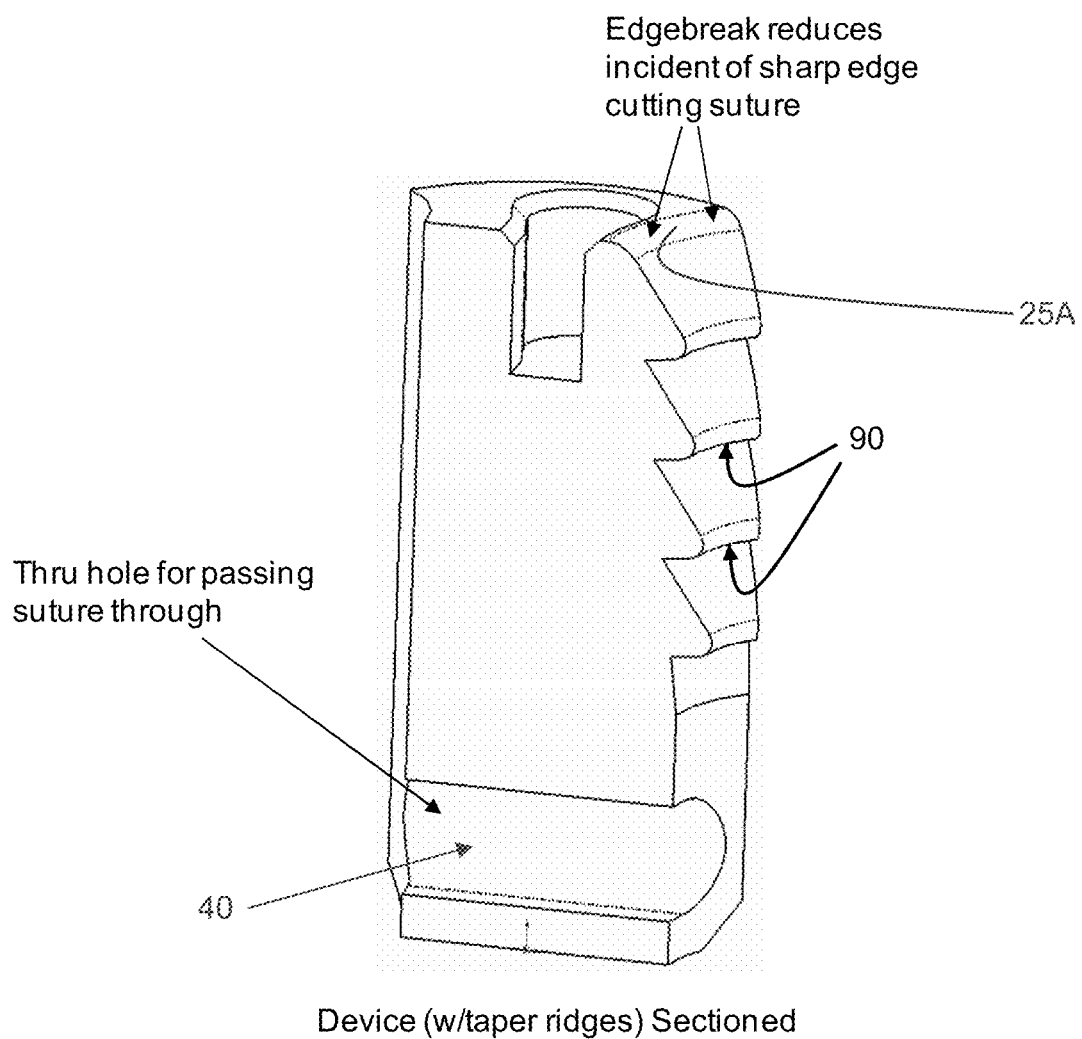

Looking next at FIGS. 18-20, there is shown a novel suture anchor assembly 85 also formed in accordance with the present invention. Suture anchor assembly 85 is substantially the same as suture anchor assembly 5 discussed above, and is used in substantially the same way, except that recess 35 includes a plurality of ribs 90. Ribs 90 help resist proximal movement of loop L and suture portion 65A relative to suture anchor body 10, while not resisting distal movement of loop L and suture portion 65A relative to suture anchor body 10.

In addition, as shown in FIGS. 18-20, a rounded corner 25A may be provided at the transition point between the proximal surface of the suture anchor body and recess 35 (and also recess 30, if desired) so as to soften the transition out of recess 35 (and also recess 30, if desired) and thereby reduce wear and abrasion of suture 15.

Figure 21:
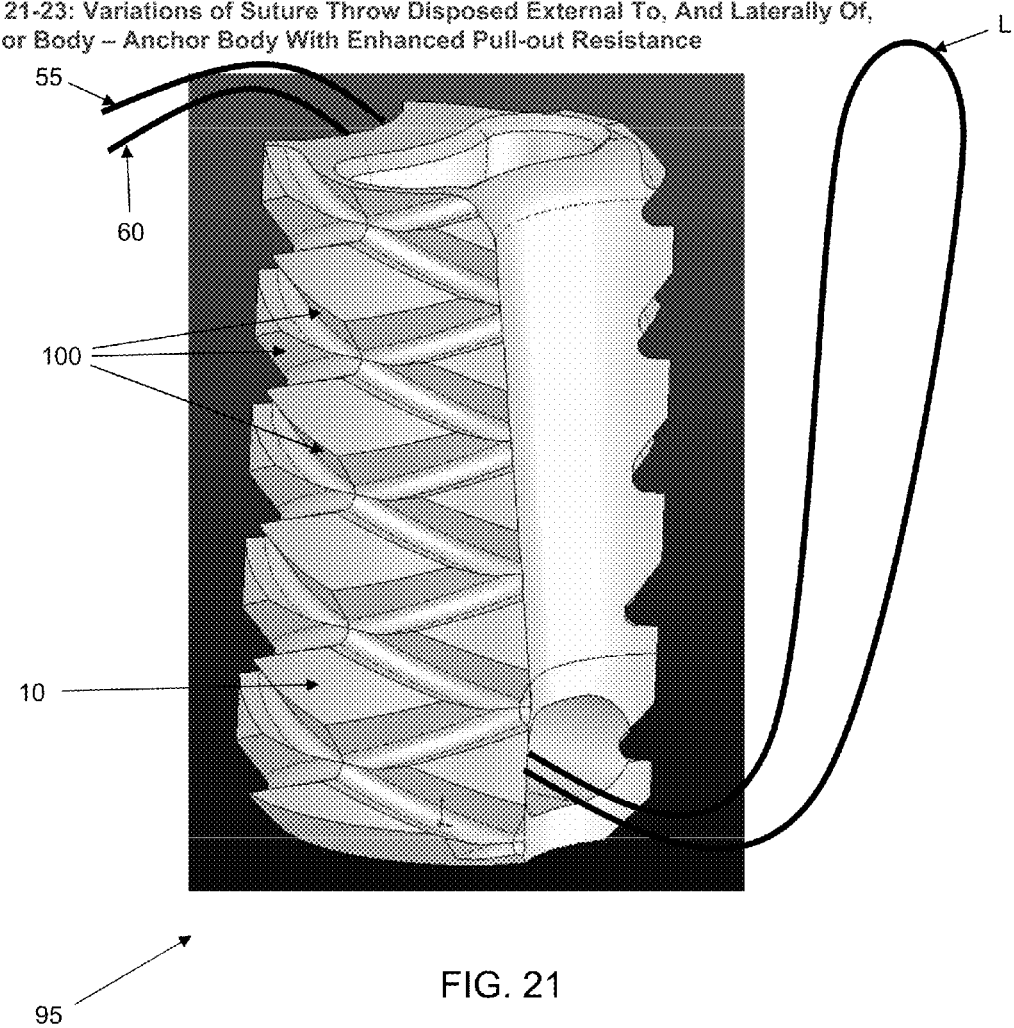
FIGS. 21-23 are schematic views showing a fifth suture anchor assembly formed in accordance with the present invention.
Figure 22:
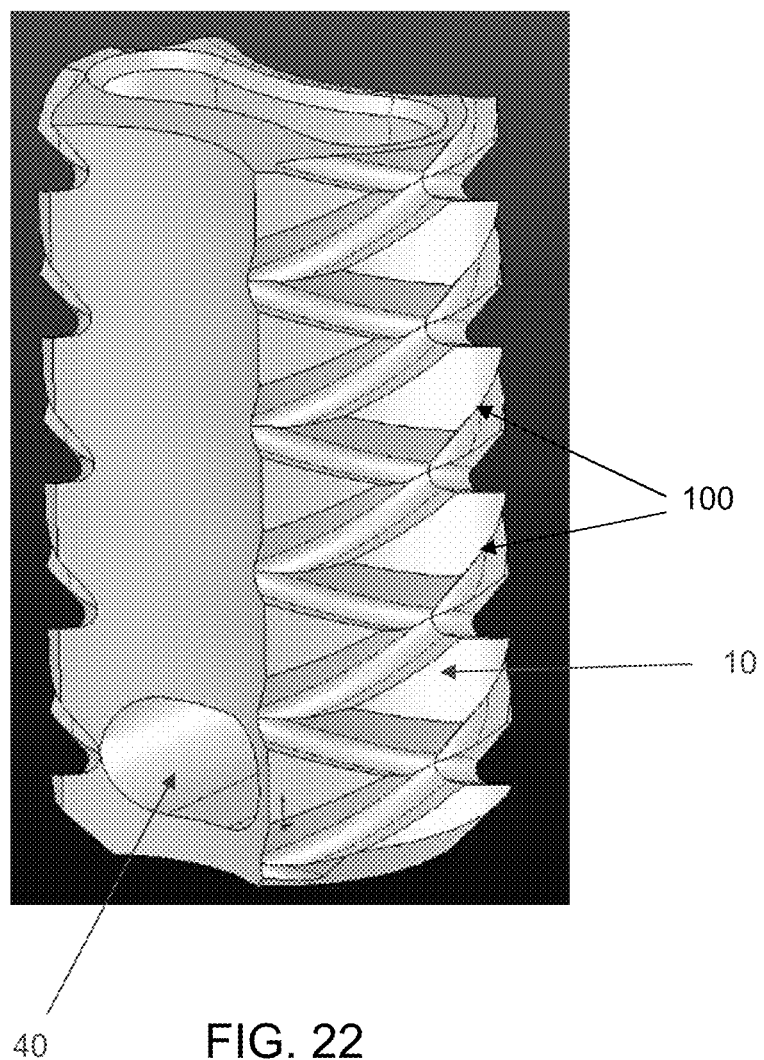
Figure 23:
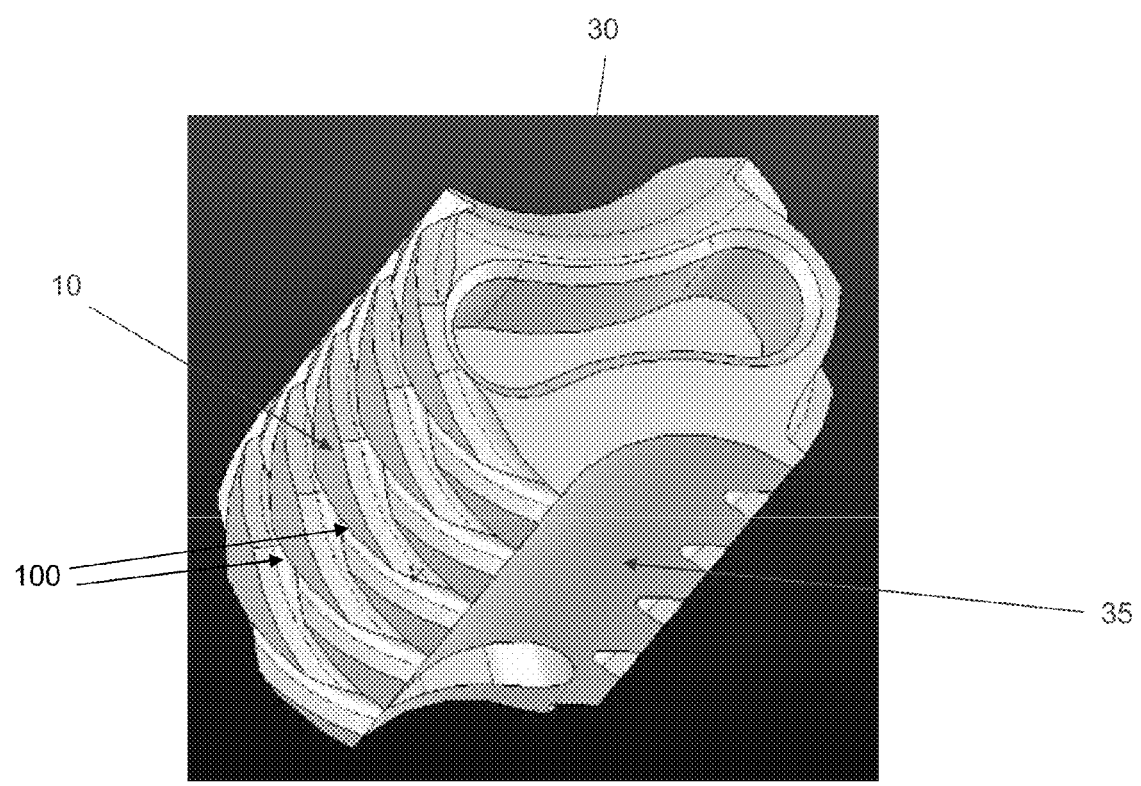

Looking next at FIGS. 21-23, there is shown a novel suture anchor assembly 95 also formed in accordance with the present invention. Suture anchor assembly 95 is substantially the same as suture anchor assembly 5 discussed above, and is used in substantially the same way, except that suture anchor body 10 comprises a plurality of surface ridges 100. Surface ridges 100 help resist proximal movement of suture anchor body 10 relative to the bone, while not resisting distal movement of suture anchor body 10 into bone hole H. In this specific embodiment, ridges 100 are formed by intersecting clockwise and counter-clockwise helical cuts. The resolution of the ridges, the ridge root width, and angle of incidence between the ridges is controlled by the pitch on the helical cuts and the number of leads. In the case where finer engagement with bone is required, a finer pitch can be used; in the case where coarser engagement with bone is required, coarser pitches may be used to increase engagement with the bone. To increase or decrease root width, less or more leads can be used to increase or decrease the distance between two adjacent cuts, accordingly.

The geometry of the cuts is important for enhancing bone engagement. As shown in FIGS. 21-23, the cuts are preferably substantially perpendicular to the body of the suture anchor on the proximal side of the ridges but are substantially tapered on the distal portion of the ridges. The perpendicular proximal side enhances gripping of the bone while the tapered distal portion facilitates slipping the device past the bone for ease of insertion into bone hole H. The geometry of the helical sweeps can be varied so as to increase grip on the bone or to ease insertion through the bone, for instance by making the proximal side of the ridge undercut relative to a perpendicular cut as shown.

Figure 24:
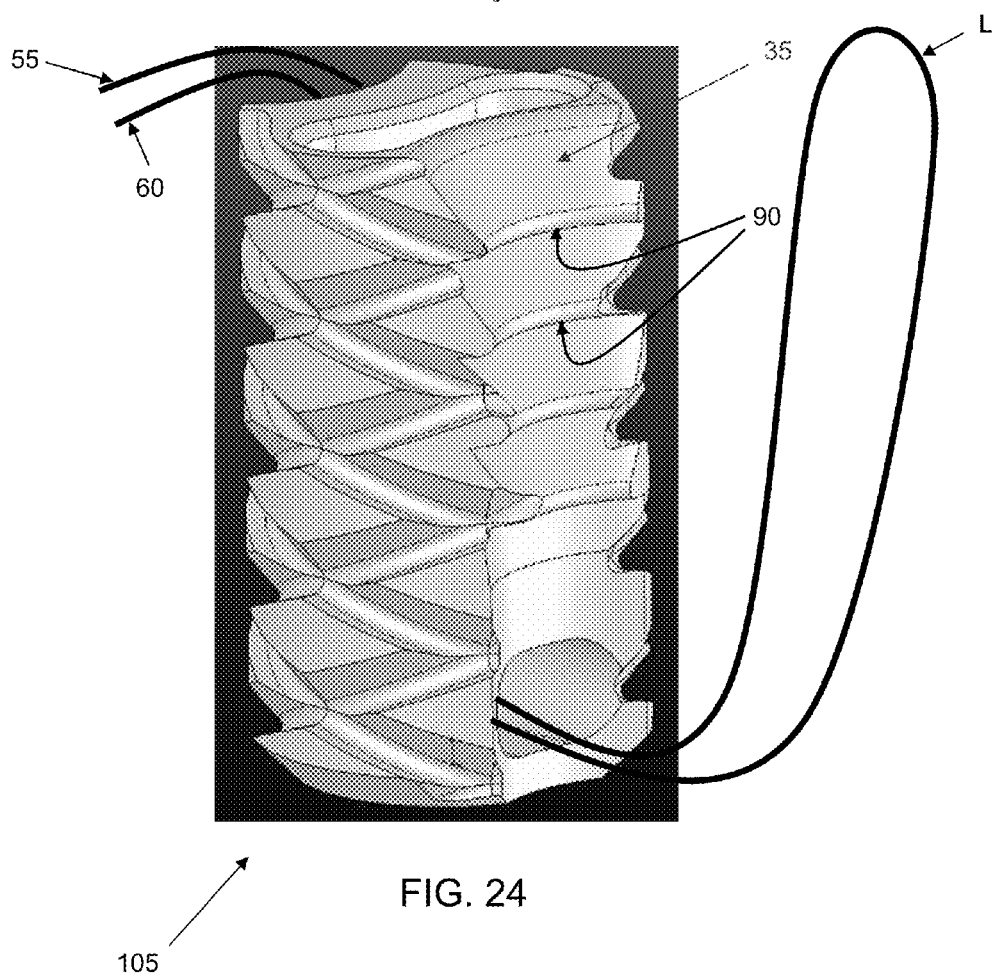
FIG. 24 is a schematic view showing a sixth suture anchor assembly formed in accordance with the present invention.

Looking next at FIG. 24, there is shown a novel suture anchor assembly 105 also formed in accordance with the present invention. Suture anchor assembly 105 is substantially the same as suture anchor assembly 95 discussed above, and is used in substantially the same way, except that ribs 90 are provided in recess 35.

Figure 25:
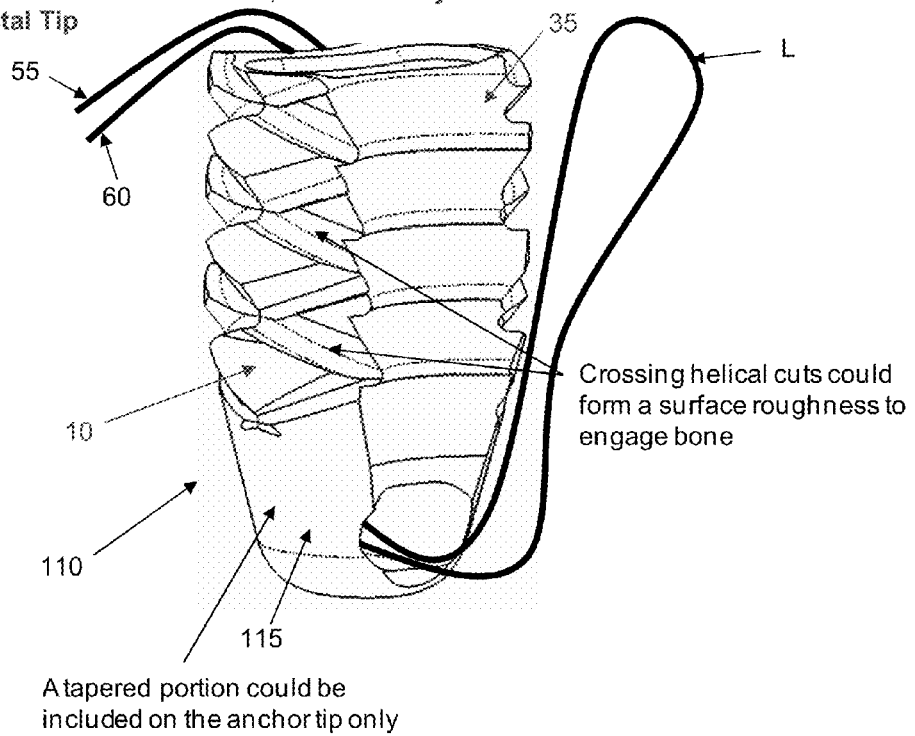
FIG. 25 is a schematic view showing a seventh suture anchor assembly formed in accordance with the present invention.
Figure 26:
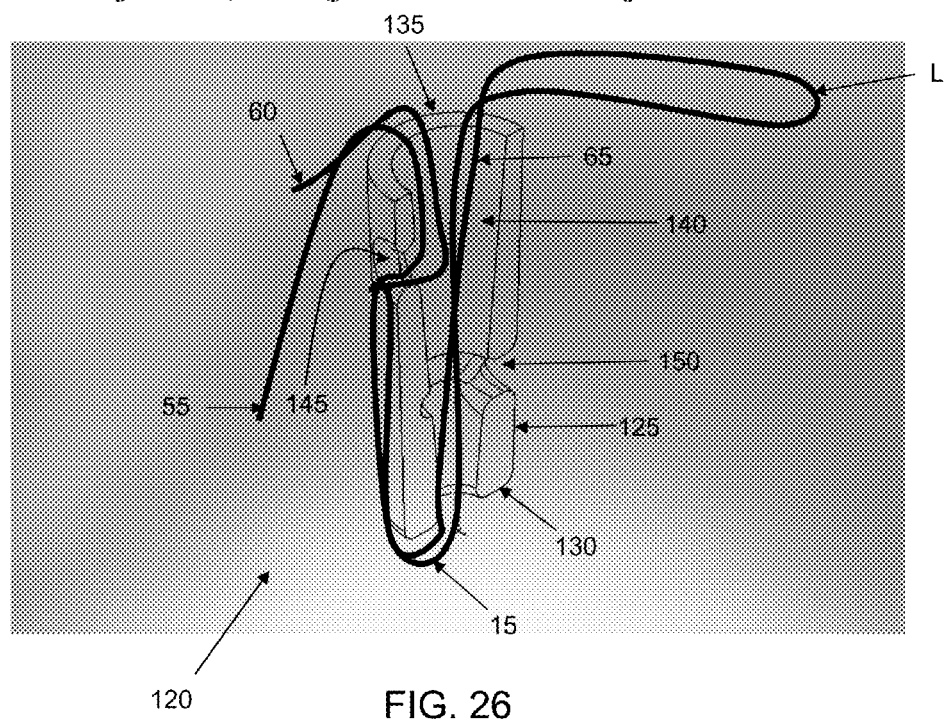
FIGS. 26-29 and 29A are schematic views showing an eighth suture anchor assembly formed in accordance with the present invention.
Figure 27:
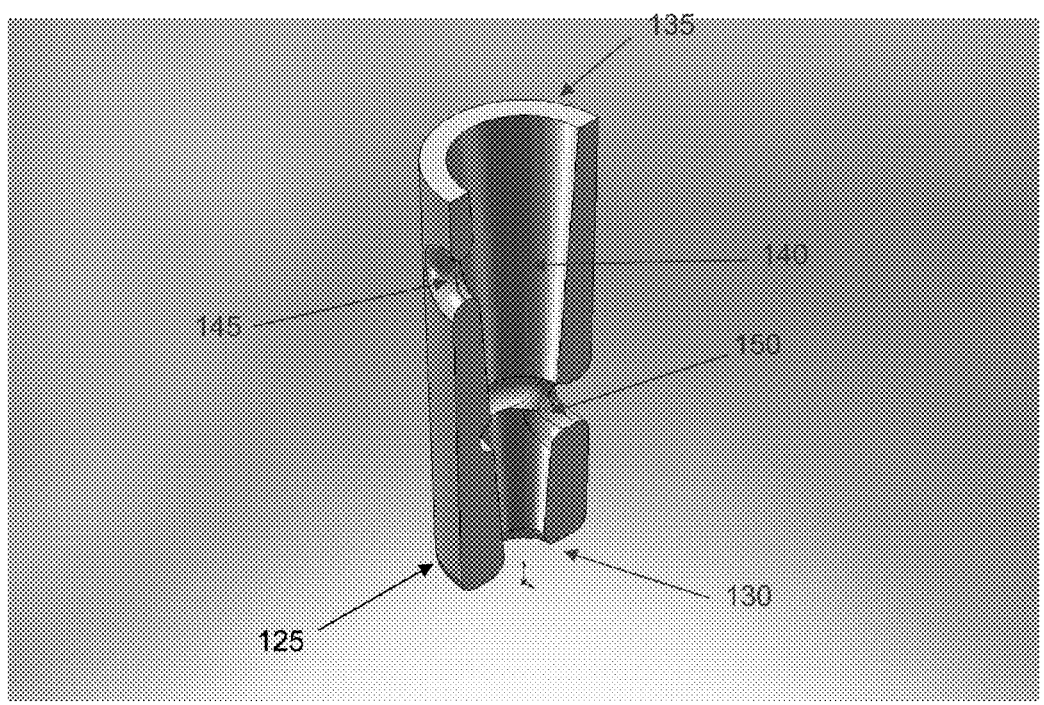
Figure 28:
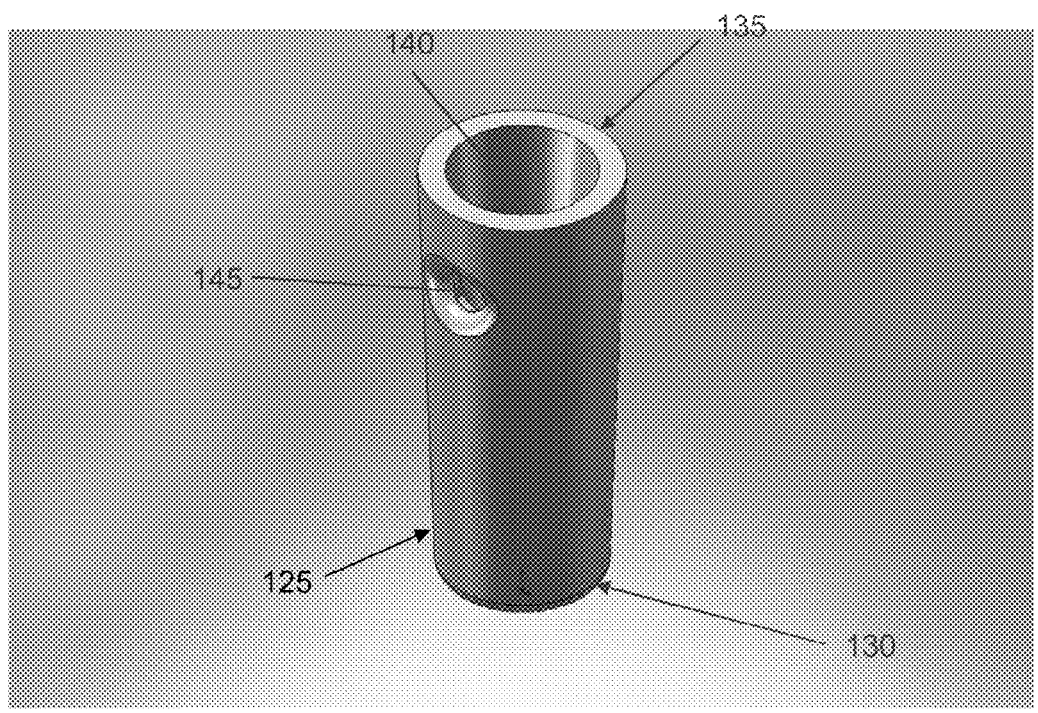
Figure 29:
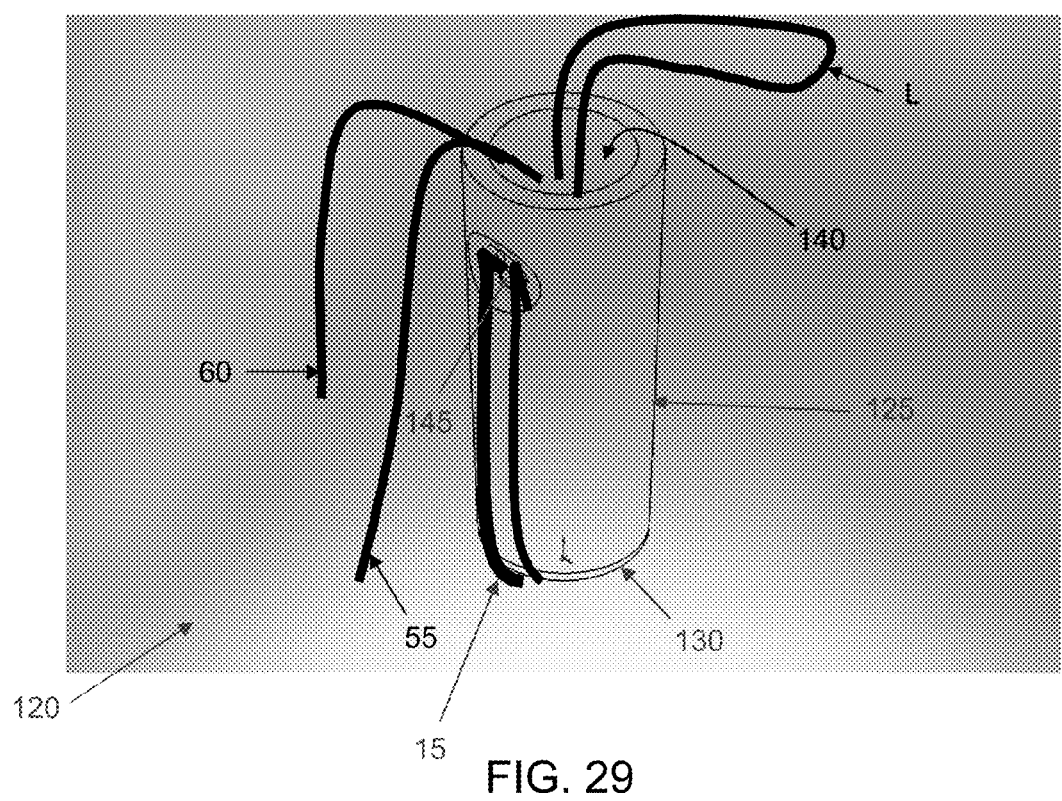
Figure 29A:
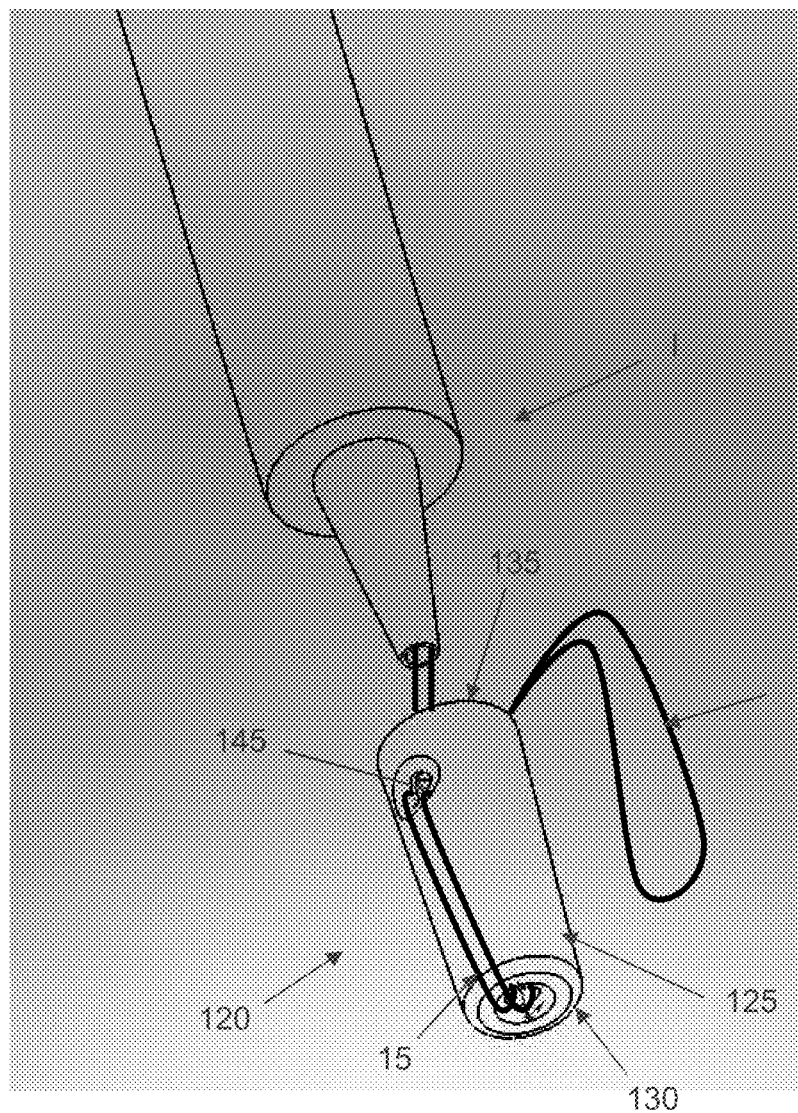
Figure 30:
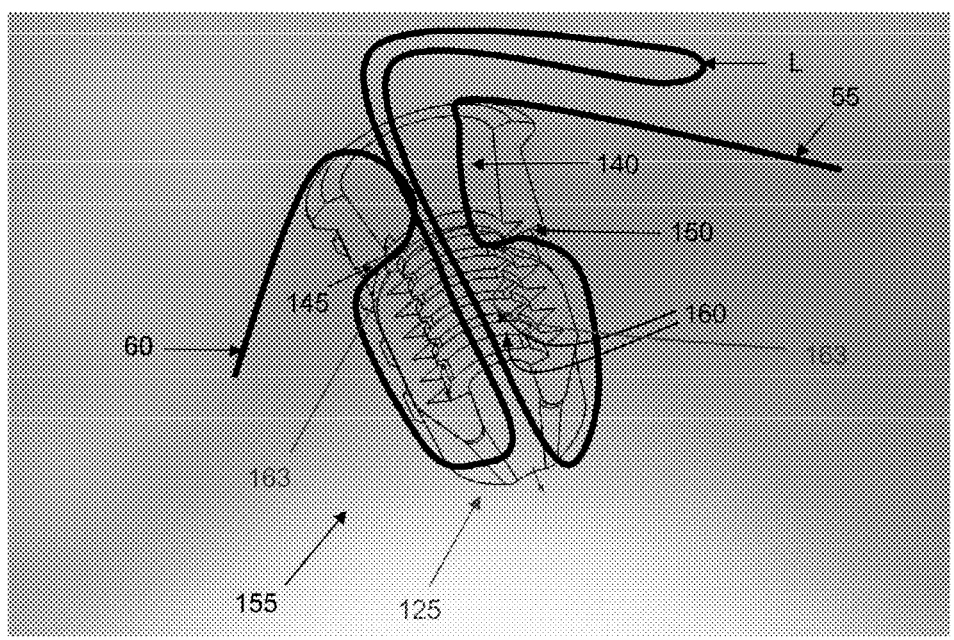
FIGS. 30-32 are schematic views showing a ninth suture anchor assembly formed in accordance with the present invention.
Figure 31:
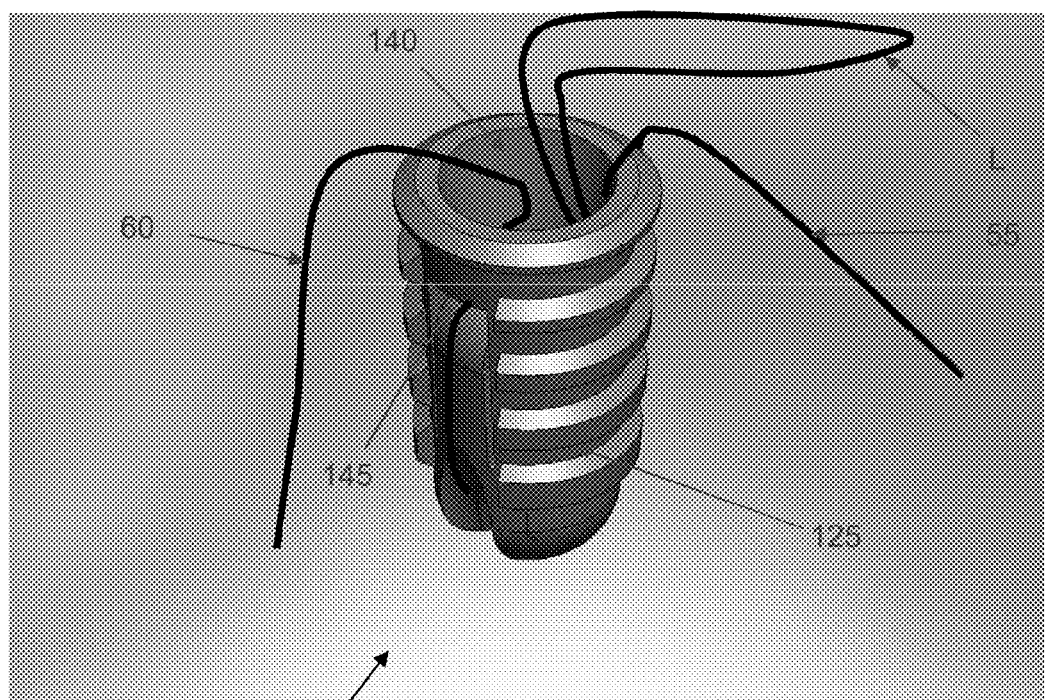
Figure 32:
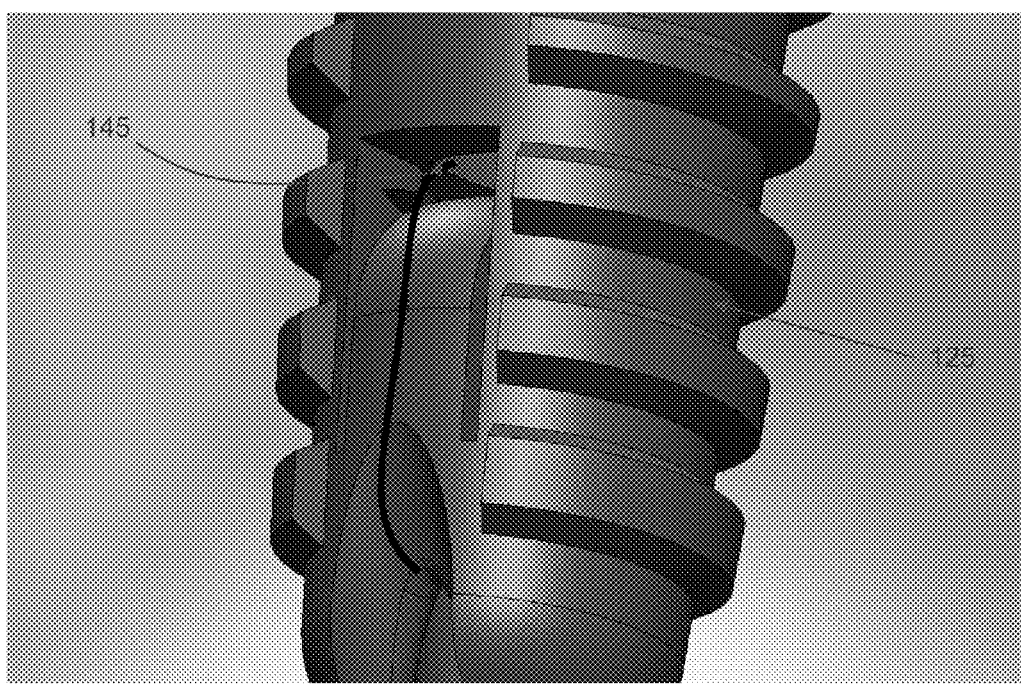

Looking next at FIG. 25, there is shown a novel suture anchor assembly 110 also formed in accordance with the present invention. Suture anchor assembly 110 is substantially the same as suture anchor assembly 105 discussed above, and is used in substantially the same way, except that it provides a rounded distal tip 115 to suture anchor body 10. This construction provides suture anchor body 10 with a distal tip which facilitates insertion into the bone hole. Of course, it is also possible to provide many other distal end geometries of the sort well known in the art to aid in the insertion of the suture anchor body into bone, e.g., such as breaking the distal end, providing a generously rounded lead-in or tapered portion, or providing any other feature that incorporates a reduced cross-section tip for more easily locating the anchor in the prepared hole.

Looking next at FIGS. 26-29 and FIG. 29A, there is shown a novel suture anchor assembly 120 also formed in accordance with the present invention. Suture anchor assembly 120 generally comprises a suture anchor body 125 and a suture 15. Suture anchor assembly 120 may be used to secure soft tissue to bone without requiring the surgeon to tie a knot (or knots) in the suture.

More particularly, suture anchor body 125 comprises a generally cylindrical structure having a distal end 130 and a proximal end 135. A tapered lumen 140 extends from distal end 130 to proximal end 135. More particularly, lumen 140 tapers inwardly as it extends distally along suture anchor body 125. Thus, and as will hereinafter be discussed in further detail, the gap between the opposing walls of tapered lumen 140 progressively narrows towards the distal end of suture anchor body 125. Preferably a side opening 145 is formed in suture anchor body 125 near the proximal end of the anchor body, and/or a side opening 150 is formed in suture anchor body 125 near the distal end of the anchor body.

It should be appreciated that the tapered portion of tapered lumen 140 may extend the entire length of tapered lumen 140 or along only a portion (or portions) of tapered lumen 140. Thus, for example, the tapered portion of tapered lumen 140 may be disposed between two cylindrical sections, or it may be located distal of a proximal cylindrical section, or it may be located proximal of a distal cylindrical section. Additionally, tapered lumen 140 could comprise a step-like combination of tapered and cylindrical portions (i.e., like stairs). These configurations can help improve sliding of suture 15 within tapered lumen 140 and to help ensure that the locking portion of the suture will come to rest adjacent to a specific section of the suture anchor body (e.g., a portion of the suture anchor body having a more substantial cross-section so as to provide increased body strength, or an area with internal features for interlocking with the suture, etc.).

As previously described, suture 15 comprises a single strand of suture having a leading end 55, a trailing end 60 and an intermediate portion 65 therebetween.

Suture anchor assembly 120 may be used as follows to secure soft tissue to bone without requiring the surgeon to tie a knot (or knots) in the suture.

More particularly, leading end 55 of suture 15 is first placed adjacent to trailing end 60 of suture 15, thereby forming a loop L in the intermediate portion 65 of suture 15. Then, leading end 55 and trailing end 60 are threaded down tapered lumen 140, out the distal end of tapered lumen 140, up the exterior of suture anchor body 125, into side opening 145, back into tapered lumen 140 and then out the proximal end of suture anchor body 125. See FIG. 26. If desired, a trough or groove may be provided on the exterior surface of suture anchor body 125 to receive the suture between openings 140 and 145. This can help protect the suture from wear and abrasion from the surrounding bone during insertion and/or during sliding of the suture (e.g., during securement and/or adjustment).

Then suture anchor assembly 120 is deployed in a bone, preferably by advancing distal end 130 of suture anchor body 125 into a hole formed in the bone. This may be done by mounting the distal end of an inserter I (FIG. 29A) into tapered lumen 140 of suture anchor body 125, simultaneously pulling a slight tension on (i) loop L and (ii) leading end 55 and trailing end 60, so that suture 15 is drawn taut around the distal end of suture anchor body 125. Then the inserter is used to push suture anchor assembly 120 into the bone hole.

Next, leading end 55 is passed over (or through) tissue and then through loop L.

Then, with leading end 55 held under tension, trailing end 60 is pulled. This action causes loop L and intermediate portion 65 of suture 15 to be drawn into, and then progressively deeper into, tapered lumen 140. However, as indicated above, the gap between the opposing walls of tapered lumen 140 (i.e., the space for receiving suture 15) progressively narrows along the length of suture anchor body 125. Thus, the more that trailing end 60 of suture 15 is pulled, the farther that loop L and suture mid-section 65 is pulled into the narrowing gap between the opposing side walls of tapered lumen 140. Pulling of trailing end 60 continues until loop L and suture mid-section 65 are effectively jammed between the opposing side walls of tapered lumen 140, thereby binding the suture at this location. This action effectively results in a fixed length of suture 15 extending from loop L, over (or through) the tissue, and then back to loop L, with loop L being locked in position relative to the anchor body and hence to the bone. Thus, by holding leading end 55 under tension and pulling trailing end 60 until loop L and the suture mid-section 65 are locked, the tissue can be secured to the bone without requiring the surgeon to tie a knot (or knots) in the suture.

If desired, suture 15 can be passed through side opening 150 instead of side opening 145. However, passing the suture external to the anchor through the more proximal opening 145 (rather than the more distal opening 150) can provide a variety of benefits, including providing additional bulk to the anchor body leading to improved anchoring to bone and smoother flow of the sutures. On the other hand, passing the sutures through the more distal opening 150 (rather than the more proximal opening 145) can help limit the exposure of the suture to the bone, thereby reducing potential damage to the suture.

It may also be beneficial to place the suture pass-thru hole (e.g., side openings 145, 150, etc.) on other locations in the anchor body so as to better protect the suture, better secure the anchor to the bone, improve the suture securement, etc.

Figure 33:
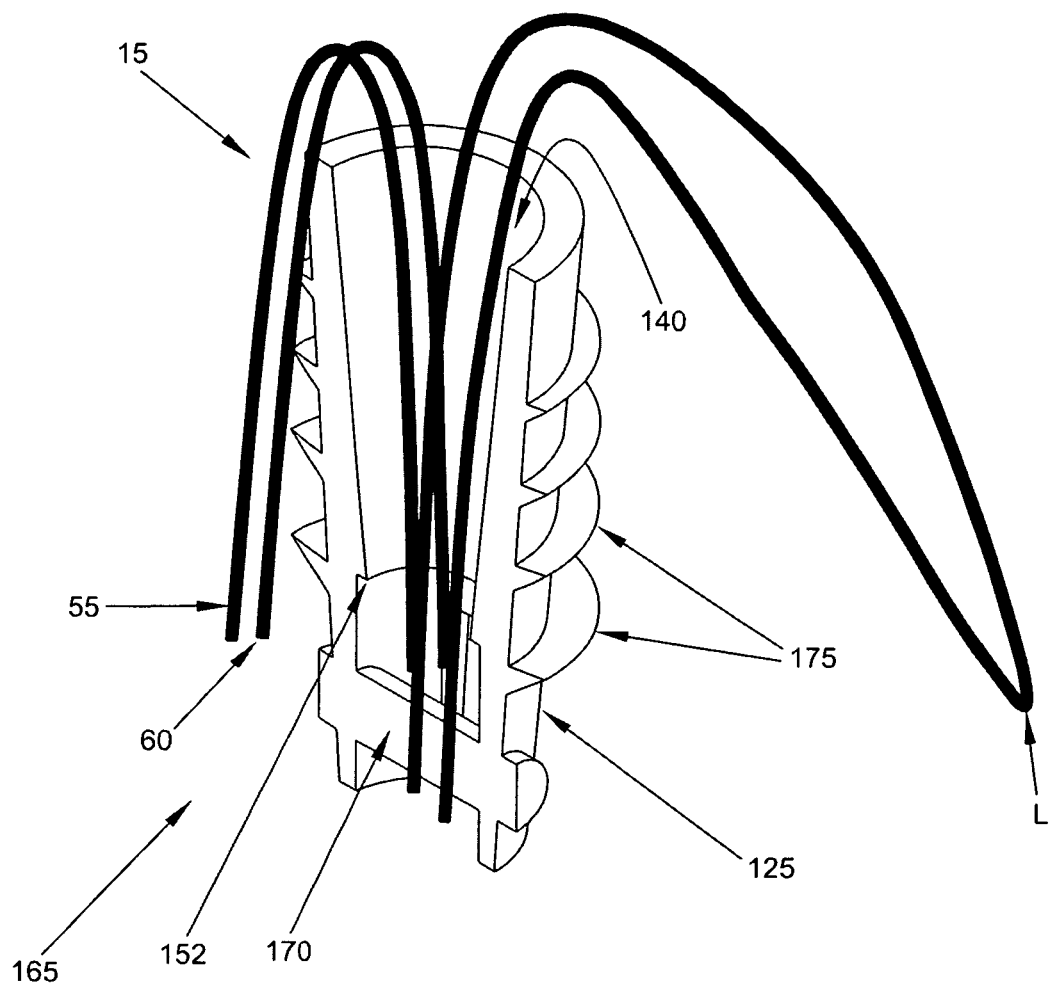
FIGS. 33, 34 and 34A-34C are schematic views showing a tenth suture anchor assembly formed in accordance with the the present invention.
Figure 34:
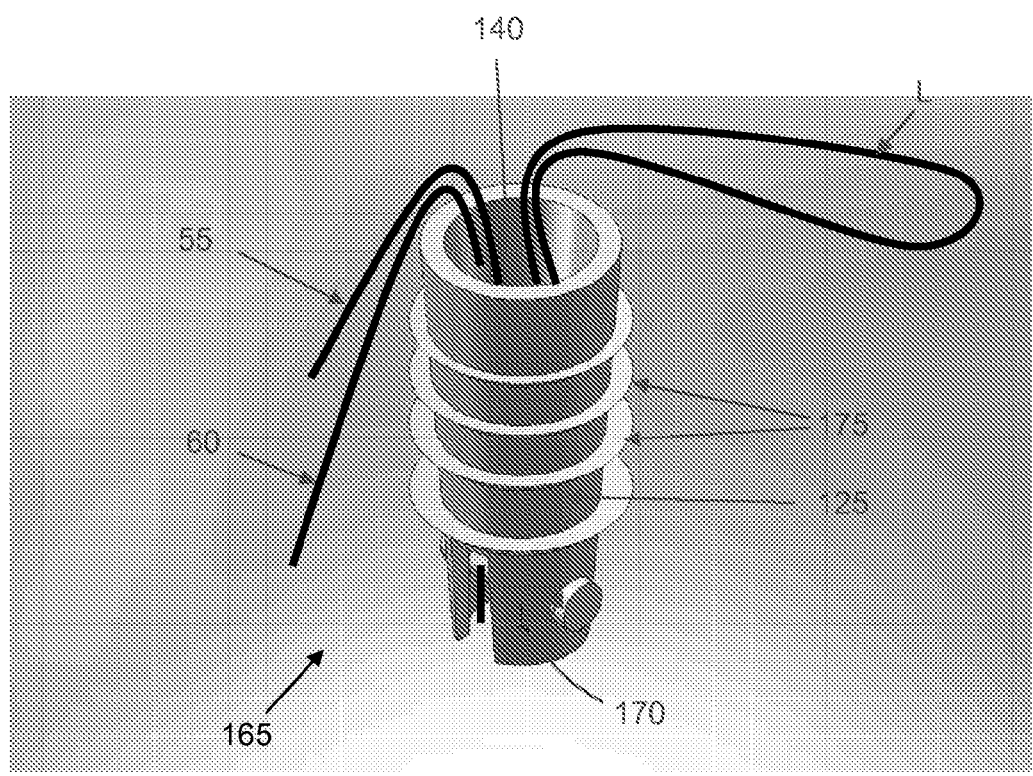

Looking next at FIGS. 33 and 34, there is shown a novel suture anchor assembly 165 also formed in accordance with the present invention. Suture anchor assembly 165 is substantially the same as suture anchor assembly 120 discussed above, except that (i) side openings 145, 150 are omitted, (ii) a crosspin 170 is formed at the distal end of tapered lumen 140, (iii) a shoulder 152 is formed within tapered lumen 140 proximal to crosspin 170, and (iv) (ribs 175 are formed on the exterior of suture anchor body 125. Furthermore, suture 15 is threaded into suture anchor body 125 by threading leading end 55 and trailing end 60 down tapered lumen 140, around crosspin 170, then back up tapered lumen 140 and out the proximal end of suture anchor body 125.

Suture anchor assembly 155 is used in substantially the same way as suture anchor assembly 120, i.e., after the suture anchor body is disposed in the bone, leading end 55 of suture 15 is passed over (or through) the tissue to be captured, through loop L and then, while leading end 55 is held under tension, trailing end 60 is pulled so as to draw loop L and a new portion of the suture mid-section 65 down tapered lumen 140 until loop L and suture mid-section 65 are locked in position. In this way, suture anchor assembly 155 can be used to secure tissue to bone without requiring the surgeon to tie a knot (or knots) in the suture. Also, as suture 15 is tensioned, it could pull inward tabs 163 that extend distal to holes 145 and 150 in suture anchor body 125, further locking suture 15 within tapered lumen 140 of the device.

Looking next at FIGS. 33 and 34, there is shown a novel suture anchor assembly 165 also formed in accordance with the present invention. Suture anchor assembly 165 is substantially the same as suture anchor assembly 120 discussed above, except that (i) side openings 145, 150 are omitted, (ii) a crosspin 170 is formed at the distal end of tapered lumen 140, (iii) a shoulder 152 is formed within tapered lumen 140 proximal to crosspin 170, and (iv) ribs 175 are formed on the exterior of suture anchor body 125. Furthermore, suture 15 is threaded into suture anchor body 125 by threading leading end 55 and trailing end 60 down tapered lumen 140, around crosspin 170, then back up tapered lumen 140 and out the proximal end of suture anchor body 125.

Figure 34A:
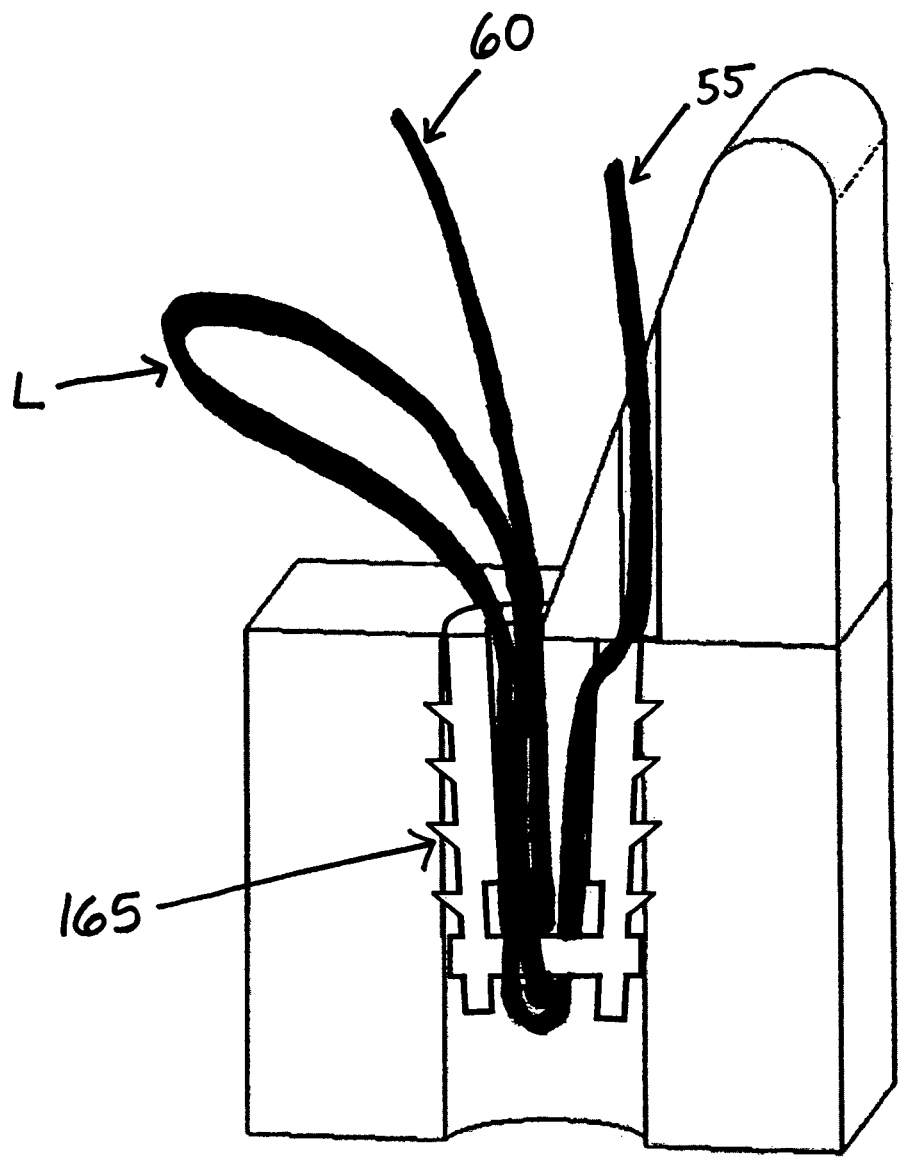
Figure 34B:
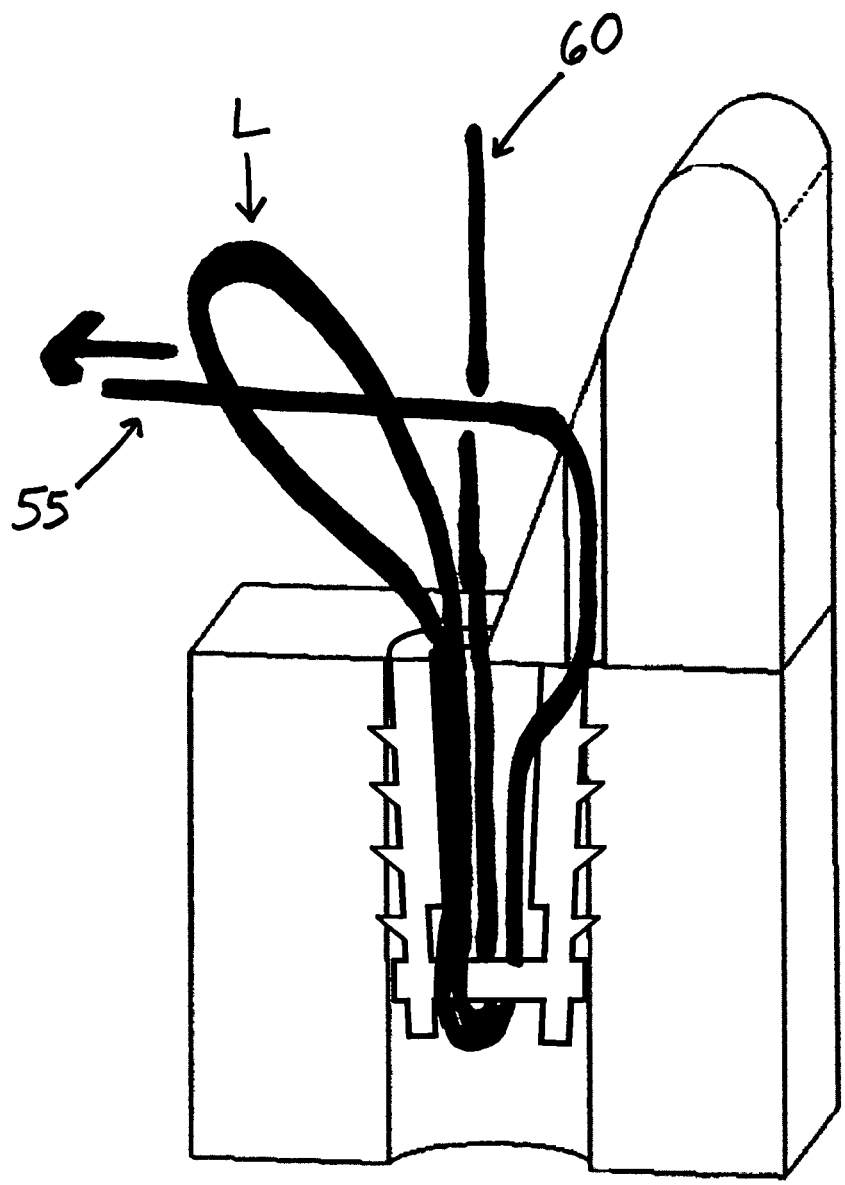
Figure 34C:
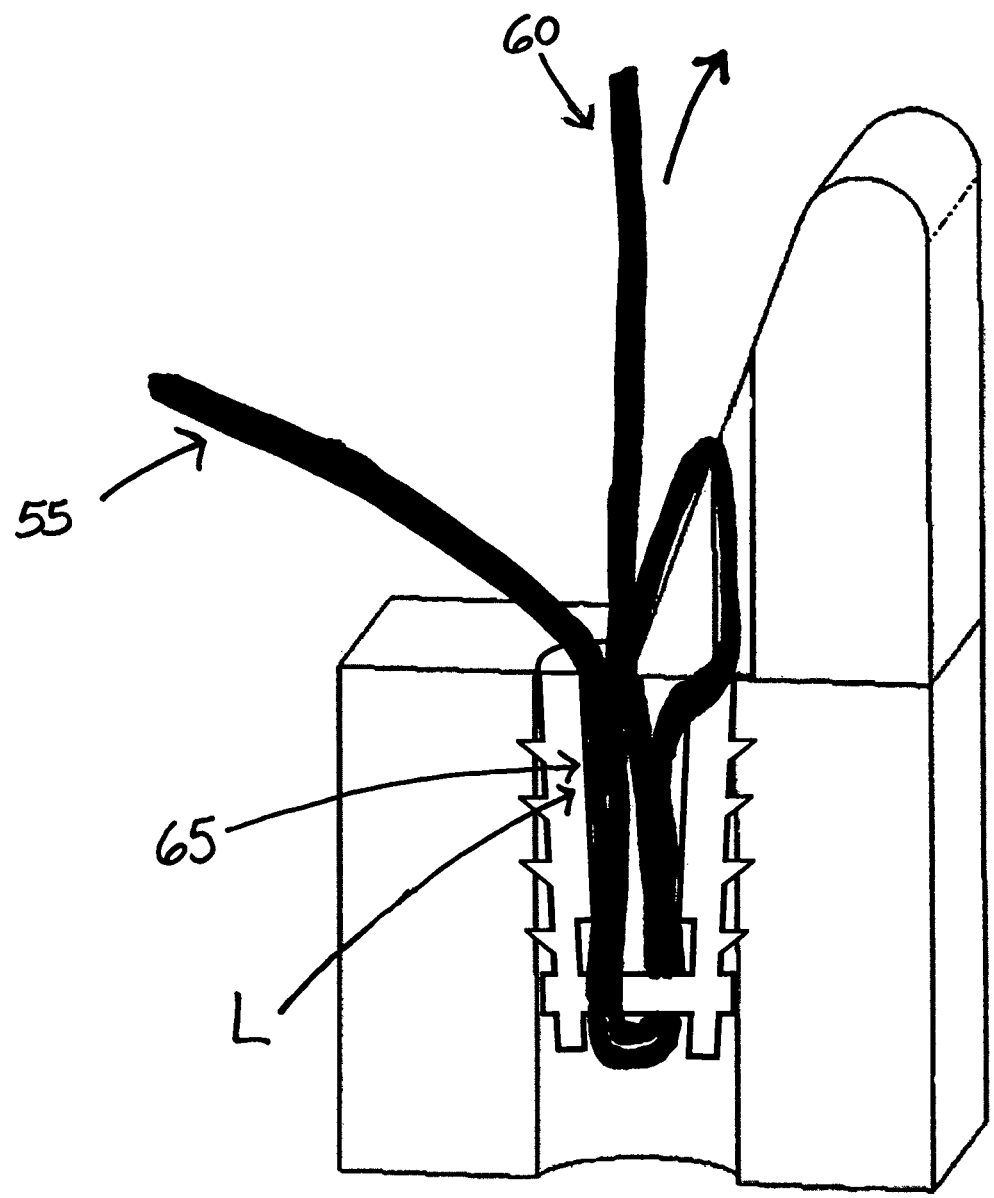

Features such as ribs 175 may be added to exterior surfaces of the suture anchor body so as to improve the grip of the suture anchor body on the bone. Other external features may also be used, e.g., threads, opposing threads, bumps, textures, ridges, discontinuous features, etc. and then, while leading end 55 is held under tension, Suture anchor assembly 165 is used in substantially the same way as suture anchor assembly 120, i.e., after the suture anchor body is disposed in the bone, leading end 55 of suture 15 is passed over (or through) the tissue to be captured (FIG. 34A), through loop L (FIG. 34B) and then, while leading end 55 is held under tension, trailing end 60 is pulled so as to draw loop L and suture mid-section 65 down tapered lumen 140 until loop L and suture mid-section 65 are locked in position (FIG. 34C). In this way, suture anchor assembly 155 can be used to secure tissue to bone without requiring the surgeon to tie a knot (or knots) in the suture.

Figure 35:
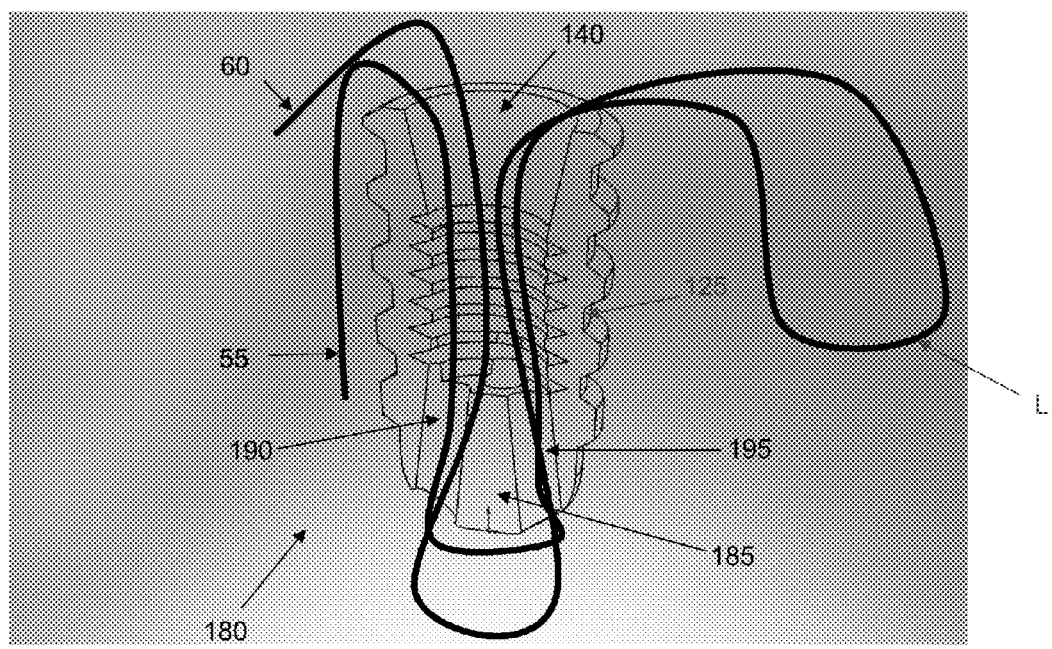
FIGS. 35 and 36 are schematic views showing an eleventh suture anchor assembly formed in accordance with the present invention.
Figure 36:
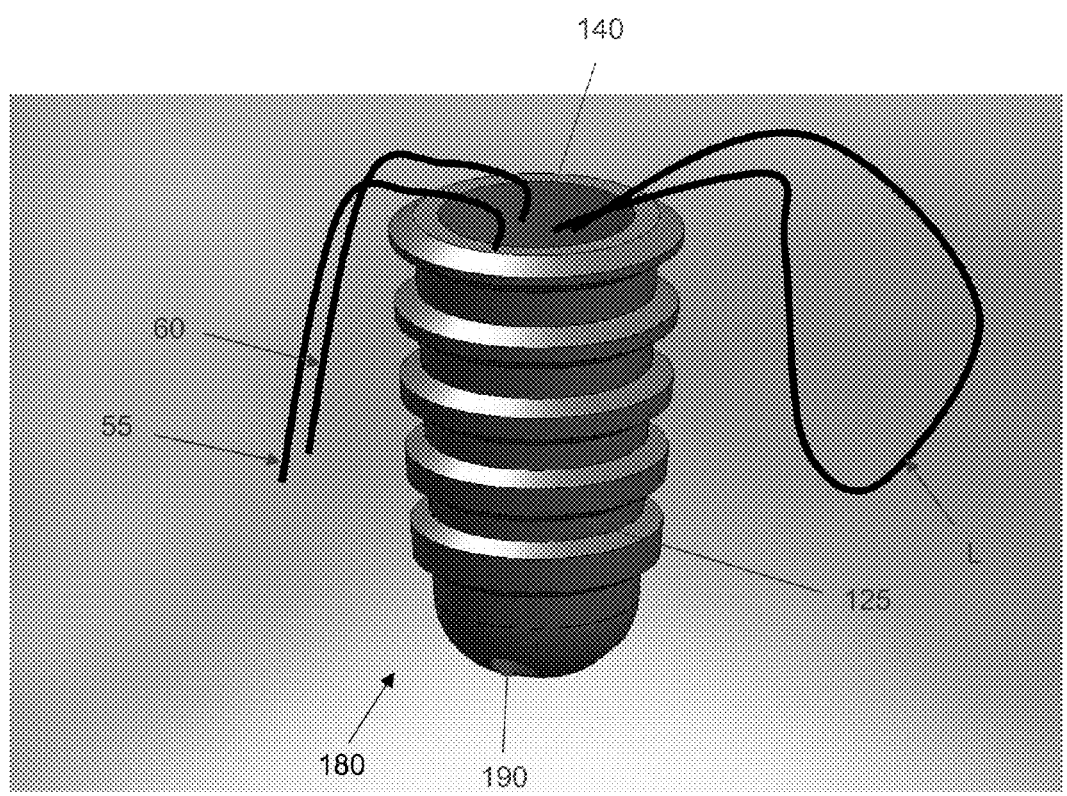
Figures 40, 41:
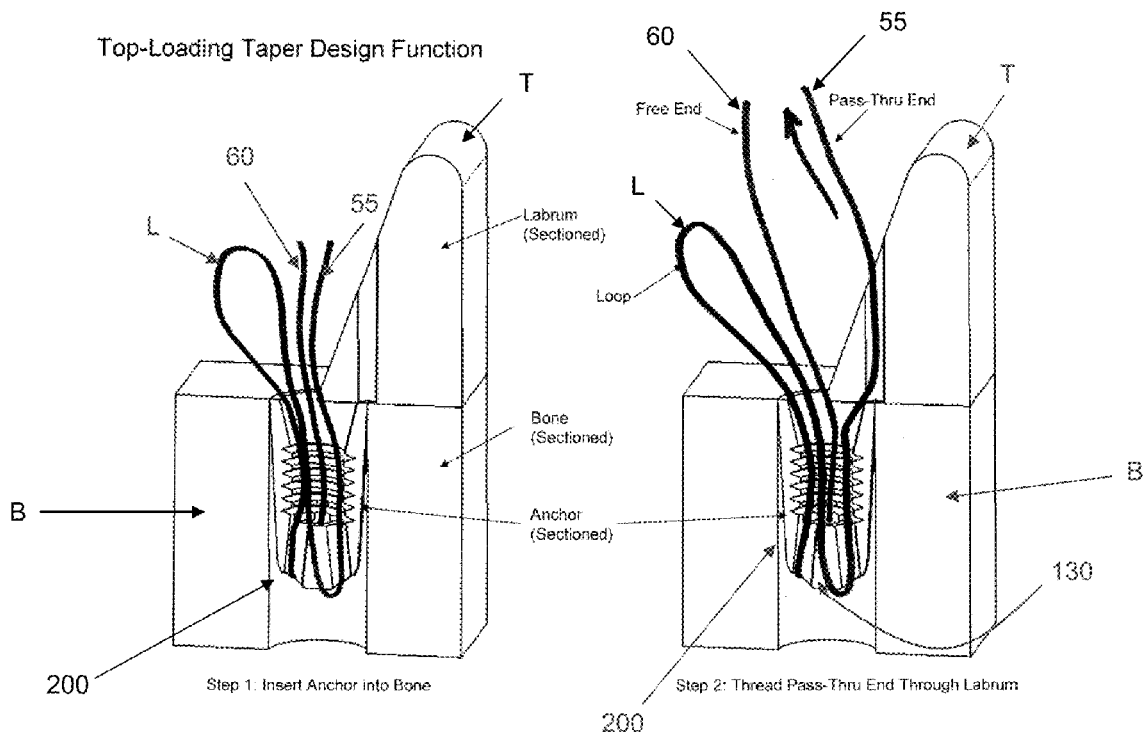

Looking next at FIGS. 35 and 36, there is shown a novel suture anchor assembly 180 also formed in accordance with the present invention. Suture anchor assembly 180 is substantially the same as suture anchor assembly 165 discussed above, except that tapered lumen 140 is a blind hole terminating proximal to the distal end of suture anchor body 125 so as to provide a distal end wall 185, and at least two openings 190, 195 are formed through the distal end wall. Furthermore, suture 15 is threaded into suture anchor body 125 by threading leading end 55 and trailing end 60 down tapered lumen 140, out of an opening (e.g., opening 195), along the exterior of the distal end wall, into an opening (e.g., opening 190), and then back up tapered lumen 140 and out the proximal end of suture anchor body 125. A trough or groove to connect openings 195 and 190 may be provided so as to protect the suture, especially during insertion into bone.

Suture anchor assembly 180 is used in substantially the same way as suture anchor assembly 165, i.e., after the suture anchor body is disposed in the bone, leading end 55 of suture 15 is passed over (or through) the tissue to be captured, through loop L and then, while leading end 55 is held under tension, trailing end 60 is pulled so as to draw loop L and suture mid-section 65 down tapered lumen 140 until loop L and suture mid-section 65 are locked in position. In this way, suture anchor assembly 155 can be used to secure tissue to bone without requiring the surgeon to tie a knot (or knots) in the suture.

Looking next at FIGS. 37-43, there is shown a novel suture anchor assembly 200 also formed in accordance with the present invention. Suture anchor assembly 200 is substantially the same as suture anchor assembly 185 discussed above, except that four openings are formed through the distal end wall, the suture follows a slightly different path, and the exterior of suture anchor body 125 may be formed without ribs. However, it should be understood that with suture anchor assembly 200 (and also with suture anchor assembly 180, etc.) there are a multitude of external features that may or may not be included for the purpose of enhancing fixation of the anchor body to bone. For example, the opposing helical cuts (such as shown in suture anchor assembly 95) are such a feature. Ribs, bumps and other texturing features may also be included. Suture anchor assembly 200 generally comprises a suture anchor body 125 and a suture 15. Suture anchor assembly 200 may be used to secure soft tissue to bone without requiring the formation of a knot (or knots).

Suture anchor body 125 comprises a generally tapered structure having a distal end 130 and a proximal end 135. A tapered lumen 140 extends from distal end 130 to proximal end 135. More particularly, tapered lumen 140 tapers inwardly as it extends distally along suture anchor body 125. Thus, and as will hereinafter be discussed in further detail, the gap between the opposing walls of tapered lumen 140 progressively narrows towards the distal end of suture anchor body 125. Preferably four openings 205, 210, 215, 220 are formed in the distal end wall of suture anchor body 125.

Suture 15 comprises a single strand of suture having a leading end 55, a trailing end 60 and an intermediate portion 65 therebetween.

More particularly, leading end 55 of suture 15 is first placed adjacent to trailing end 60 of suture 15, thereby forming a loop L in intermediate portion 65 of suture 15. Then, leading end 55 is passed down tapered lumen 140, out of opening 205, across the exterior of the distal end wall, into opening 210, back up tapered lumen 140 and then out the proximal end of suture anchor body 125. Then, trailing end 60 is passed down tapered lumen 140, out of opening 215, across the exterior of the distal end wall, into opening 220, back up tapered lumen 140 and then out the proximal end of suture anchor body 125. See FIG. 38.

Then suture anchor assembly 200 is deployed in a bone, preferably by advancing distal end 130 of suture anchor assembly 200 into a hole formed in the bone. This may be done by mounting the distal end of an inserter (not shown)

into tapered lumen 140 of suture anchor body 125, pulling a slight tension on loop L, and leading end 55 and trailing end 60, so that suture 15 is drawn taut around the distal end of suture anchor body 125. Then the inserter is used to push suture anchor assembly 200 into the bone hole. See FIG. 40.

Next, leading end 55 is passed over (or through) tissue T (see FIG. 41) and then through loop L (see FIG. 42).

Then, with leading end 55 held under tension, trailing end 60 is pulled. This action causes loop L and intermediate portion 65 to be drawn into, and then progressively deeper into, tapered lumen 140 which has progressively narrowing cross-section. See FIG. 43. The more that trailing end 60 is pulled, the farther that loop L and suture mid-section 65 are pulled into the narrowing gap between the opposing side walls of tapered lumen 140 eventually jamming all of the suture between the opposing side walls of tapered lumen 140, thereby binding the suture at this location. This action effectively results in a fixed length of suture 15 extending from loop L, over (or through) tissue T, and then back to loop L, with loop L being locked in position relative to the anchor body and hence the bone. Thus, by holding leading end 55 under tension and pulling trailing end 60 until loop L and suture mid-section 65 are locked, tissue T can be secured to the bone without requiring the surgeon to tie a knot (or knots) in the suture.

Thus it will be seen that the present invention provides a novel suture anchor which may be used to secure soft tissue to bone without requiring the surgeon to tie a knot (or knots) in the suture.

Clinical Applications

In the foregoing discussion, the present invention is discussed in the general context of being used to secure soft tissue to bone.

In preferred clinical applications, the present invention may be used to secure a ligament to bone, a tendon to bone, a labrum to the acetabulum, etc. In essence, the present invention may be used to secure substantially any soft tissue to any bone.

It should also be appreciated that the present invention may be used to secure objects other than soft tissue to bone. By way of example but not limitation, the present invention may be used to secure an implant to bone.

Thus it will be seen that the present invention may be used to secure substantially any object to substantially any bone.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for securing an object to bone, the method comprising:
    providing an apparatus comprising:
        a suture anchor assembly comprising a suture anchor body and a single strand of suture;
        the suture anchor body comprising a proximal end, a distal end, and a tapered lumen extending from the proximal end to the distal end, wherein the suture anchor body further comprises a crosspin at the distal end of the tapered lumen;
        the single strand of suture having a first end, a second end and an intermediate portion extending therebetween;
        the single strand of suture extending through the tapered lumen and around the crosspin so that the intermediate portion forms a loop exiting the proximal end of the tapered lumen and the first and second ends exit the proximal end of the tapered lumen;
    lockingly positioning the suture anchor body within a hole formed in a bone;
    passing the first end of the single strand of suture through the object;
    passing the first end of the single strand of suture exiting the object through the loop formed in the intermediate portion of the single strand of suture; and
    holding the first end of the single strand of suture under tension and pulling on the second end of the single strand of suture so as to draw the loop, and the portion of the suture passed through the loop, into the tapered lumen of the suture anchor body, thereby causing the loop and the portion of the suture passed through the loop to be jammed tightly in the tapered lumen of the suture anchor body, whereby to bind the suture, and hence the object, to the suture anchor body.

2. A method according to claim 1 wherein the suture anchor body is tapered from the proximal end to the distal end.

3. A method according to claim 1 wherein the suture anchor body comprises, a longitudinal axis extending between the distal end and the proximal end, and further wherein the tapered lumen extends substantially parallel to the longitudinal axis of the suture anchor body.

4. A method according to claim 1 wherein the suture anchor body comprises surface structures to help lock the suture anchor body within the hole formed in the bone.

5. A method according to claim 4 wherein the surface structures comprise ribs.

6. A method according to claim 1 wherein the side wall of the hole in the bone is tapered from a proximal end to a distal end.

7. A method according to claim 1 wherein the object comprises soft tissue.

8. A method according to claim 7 wherein the soft tissue comprises at least one from the group consisting of a ligament, a tendon and a labrum.

9. A method according to claim 1 wherein the apparatus further comprises an inserter for positioning the suture anchor assembly in the hole in the bone.

10. A method according to claim 1 wherein the tapered lumen in the suture anchor body comprises a shoulder.

11. A method according to claim 10 wherein the portion of the tapered lumen distal to the shoulder is wider than the portion of the tapered lumen proximal to the shoulder.

12. A method according to claim 1 wherein a constricting volume portion is established within the tapered lumen along the path followed by the loop and the portion of suture passed through the loop, so that when the second end of the suture is pulled, the loop and the portion of suture passed through the loop are drawn into the constricting volume portion, whereby to bind on themselves and lock the suture in place.

13. A method according to claim 12 wherein, when the second end of the suture is pulled, a successively decreasing cross-sectional area of the constricting volume portion causes the loop and the portion of the suture passed through the loop to be jammed tightly in the decreasing cross-sectional area, whereby to bind the suture, and hence the object, to the suture anchor body, wherein the suture anchor body is lockingly disposed within the bone.

\* \* \* \* \*